(12) United States Patent
Carroll et al.

(10) Patent No.: US 6,559,159 B2
(45) Date of Patent: May 6, 2003

(54) KAPPA OPIOID RECEPTOR LIGANDS

(75) Inventors: F. Ivy Carroll, Durham, NC (US); James B. Thomas, Efland, NC (US); S. Wayne Mascarella, Hillsborough, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 58 days.

(21) Appl. No.: 09/774,566

(22) Filed: Feb. 1, 2001

(65) Prior Publication Data

US 2002/0143145 A1 Oct. 3, 2002

(51) Int. Cl.$^7$ .......................... A61K 31/44; A61P 25/28; C07K 17/00; C07D 401/00; C07D 221/00
(52) U.S. Cl. ........................ 514/282; 514/299; 530/350; 544/60; 544/127; 544/362; 546/44; 546/45; 546/46; 546/112
(58) Field of Search ................................. 514/282, 299; 546/44–46, 112; 530/350; 544/60, 127, 362

(56) References Cited

U.S. PATENT DOCUMENTS 4,278,797 A    7/1981   Zimmerman ................ 546/112

OTHER PUBLICATIONS

J. V. Aldrich, Burger's Medicinal Chemistry and Drug Discovery, vol. 3, pp. 321–441, "Analgesics", 1996.
C. M. Bertha, et al., J. Med. Chem., vol. 39, No. 10, pp. 2081–2086, "Probes for Narcotic Receptor-Mediated Phenomena. 21. Novel Derivatives of 3–(1,2,3,4,5, 11–Hexahydro–3–methyl–2,6–methano–6H–azocino[4, 5–b]indol–6–yl)Phenols with improved δ Opioid Receptor Selectivity", 1996.
D. S. Bruce, et al., Pharmacology Biochemistry and Behavior, vol. 53, No. 4, pp. 885–889, "Circannual Variations In–Bear Plasma Albumin and its Opioid–Like Effects on Guinea Pig Ileum", 1996.
Y. Chen, et al., Molecular Pharmacology, vol. 44, pp. 8–12, "Accelerated Communication: Molecular Cloning and Functional Expression of a μ–Opioid Receptor From Rat Brain", 1993.
A. D. Corbett, et al., Nature, vol. 299, pp. 79–81, "Dynorphin$_{1-8}$ and dynorphin$_{1-9}$ are Ligands for the κ–Subtype of Opiate Receptor", Sep. 1982.
C. J. Evans, et al., Science, vol. 258, pp. 1952–1955, "Cloning of a Delta Opioid Receptor by Functional Expression", Dec. 1992.
X.–P. Gu, et al., Synthesis, pp. 535–537, "Catalytic Acetonylation of Cyclic 1,3–Dicarbonyl–Systems by 2–(Chloromethyl)–3,5–dioxa–1–hexene", Jul. 1988.
X.–P. Gu, et al., J. Org. Chem., vol. 52, No. 15, pp. 3192–3196, "2–(Chloromethyl)–3,5–dioxahex–1–ene. An Effective Acetonylating Reagent", 1987.

X.–P. Gu, et al., J. Org. Chem., vol. 51, No. 26, pp. 5425–5427, "2–Chloro–1–(chloromethyl)ethyl methoxymethyl Ether as a Reagent for Acetonylation of Alcohols and Phenol", 1986.
R. M. Jones, et al., Journal of Medicinal Chemistry, vol. 41, No. 25, pp. 4911–4914, "Mutational Evidence for a Common κ Antagonist Binding Pocket in the Wild–Type κ and Mutant μ [K303E] Opioid Receptors", Dec. 3, 1998.
B. L. Kieffer, et al., Proc. Natl. Acad. Sci., vol. 89, pp. 12048–12052, "The δ–opioid Receptor: Isolation of a cDNA by Expression Cloning and Pharmacological Characterization", Dec. 1992.
A. F. Abdel–Magid, et al., J. Org. Chem., vol. 61, No. 11, pp. 3849–3862, "Reductive Amination of Aldehydes and Ketones With Sodium Triacetoxyborohydride. Studies on Direct and Indirect Reductive Amination Procedures", 1996.
Á. Márki, et al., European Journal of Pharmacology, vol. 383, pp. 209–214, "μ–opioid Receptor Specific Antagonist Cyprodime: Characterization by In Vitro Radioligand and [$^{35}$S]GTPγS Binding Assays", 1999.
F. Meng, et al., Proc. Natl. Acad. Sci., vol. 90, No. 21, pp. 9954–9958, "Cloning and Pharmacological Characterization of a Rat κ opioid Receptor", Nov. 1993.
M. Minami, et al., FEBS 12907, vol. 329, No. 3, pp. 291–295, "Cloning and Expression of a cDNA for the Rat κ–opioid Receptor", Aug. 1993.
M. Nishi, et al., FEBS 12937, vol. 330, No. 1, pp. 77–80, "cDNA Cloning and Pharmacological Characterization of an Opioid Receptor with High Affinities for κ–Subtype–Selective Ligands", Sep. 1993.
S. L. Olmsted, et al., J. Med. Chem., vol. 36, No. 1, pp. 179–180, "A Remarkable Change of Opioid Receptor Selectivity on the Attachment of a Peptidomimetic κ Address Element to the δ Antagonist, Natrindole: 5'–[$N^2$–Alkylamidino)methyl]Naltrindole Derivatives as a Novel Class of κ Opiod Receptor Antagonists", 1993.
C. B. Pert, et al., Science, vol., 179, pp. 1011–1014, "Opiate Receptor: Demonstration in Nervous Tissue", Mar. 9, 1973.
P. S. Portoghese, IL Farmaco, vol. 48, No. 2, pp. 243–251, "The Design of δ–Selective Opioid Receptor Antagonists", 1993.
P. S. Portoghese, et al., Life Sciences, vol. 40, No. 13, pp. 1287–1292, "Binaltorphimine and Nor–Binaltorphimine, Potent and Selective κ–Opioid Receptor Antagonists", 1987.
R. Schwyzer, Annals New York Academy of Sciences, vol. 297, pp. 3–26, "ACTH: A Short Introductory Review", 1977.

(List continued on next page.)

Primary Examiner—Mukund J. Shah
Assistant Examiner—Tamthom N. Truong

(57) ABSTRACT

Structurally novel kappa opioid receptor antagonists are provided and the use of these antagonists in treatment of disease states that are ameliorated by binding of the kappa opioid receptor such as heroin or cocaine addictions.

24 Claims, 2 Drawing Sheets

OTHER PUBLICATIONS

Figure 1:
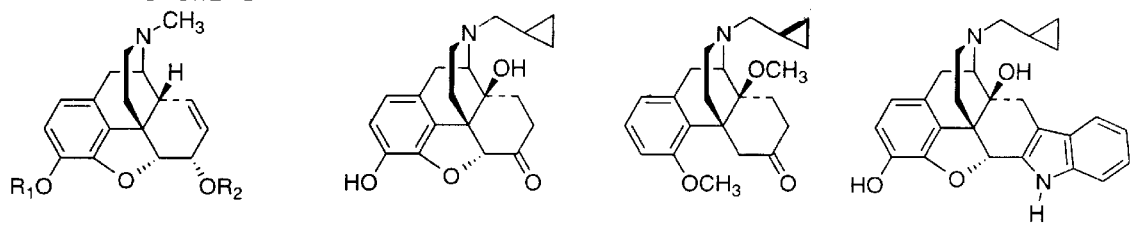
Figure 1:
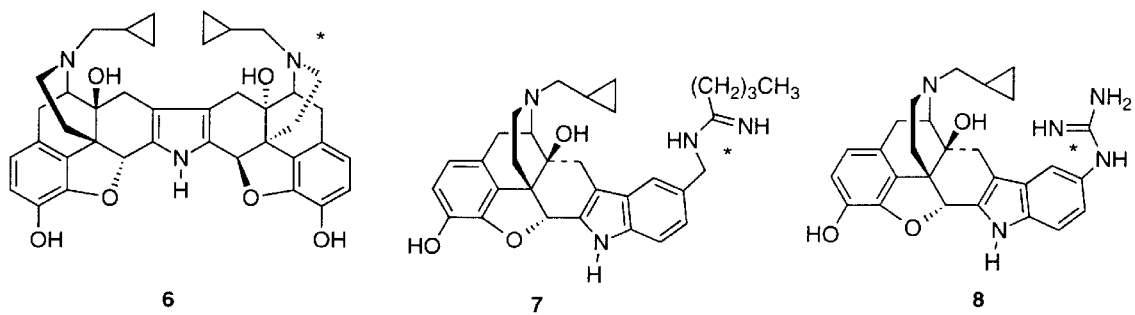
Figure 1:
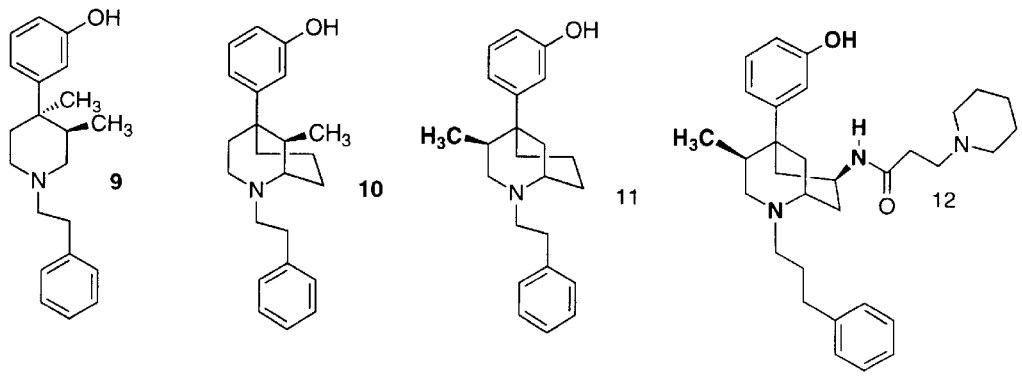
Figure 1:
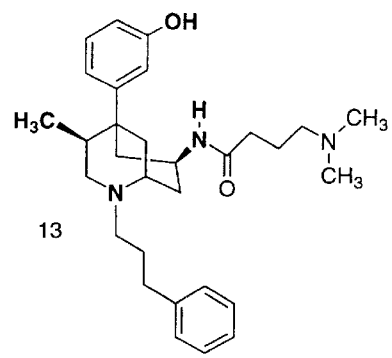

P. L. Smiley, et al., The Journal of Pharmacology and Experimental Therapeutics, vol. 253, No. 3, pp. 938–943, "Effects of Cocaine on Extrapyramidal and Limbic Dynorphin Systems", 1990.

R. Spanagel, et al., Neuroscience Letters, vol. 153, pp. 232–236, "Modulation of Morphine–Induced Sensitization by Endogenous κ Opioid Systems in the Rat", 1993.

R. Spanagel, et al., Proc. Natl. Acad. Sci., vol. 89, pp. 2046–2050, "Opposing Tonically Active Endogenous Opiod Systems Modulate the Mesolimbic Dopaminergic Pathway", Mar. 1992.

J. B. Thomas, et al., Tetrahedron Letters, vol. 40, No. 3, pp. 403–406, "A Stereoselective Synthetic Approach to N–alkyl–4β–Methyl–5–Phenymorphans", 1999.

J. B. Thomas, et al., J. Med. Chem., vol. 41, No. 11, pp. 1980–1990, "Investigation of the N–Substituent Conformation Governing Potency and $\mu$ Receptor Subtype–Selectivity in (+)–(3$R$, 4$R$)–Dimethyl–4–(3–hydroxyphenyl)–Piperdine Opioid Antagonists", 1998.

J. B. Thomas, et al., Journal of Medicinal Chemistry, vol. 41, No. 21, pp. 4143–4149, "N–Substituted 9β–methyl–5–(3–hydroxyphenyl)morphans are Opioid Receptor Pure Antagonists", 1998.

R. C. Thompson, et al., Neuron, vol. 11, No. 5, pp. 903–913, "Cloning and Pharmacological Characterization of a Rat v Opioid Receptor", Nov. 1993.

K. A. Trujillo, et al., Problems of Drug Dependence 1989: Proceedings of the 51$^{st}$ Annual Scientific Meeting, pp. 550–551, "Changes in Prodynorphin Peptide Content Following Treatment With Morphine or Amphetamine: Possible Role in Mechanisms of Action of Drug Abuse", 1989.

J. R. Volpicelli, et al., Am. J. Psychiatry, vol. 152, No. 4, pp. 613–615, "Effects of Naltrexone on Alcohol "High" in Alcoholics", Apr. 1995.

J. R. Volpicelli, et al., Arch. Gen. Psychiatry, vol. 49, pp. 876–880, "Naltrexone in the Treatment of Alcohol Dependence", Nov. 1992.

J.– B. Wang, et al., FEBS Letters, vol. 338, pp. 217–222, "Human $\mu$ Opiate Receptor: cDNA and Genomic Clones, Pharmacologic Characterization and Chromosomal Assignment", 1994.

J. A. Werner, et al., J. Org. Chem., vol. 61, pp. 587–597, "Synethis of Trans3, 4–dimethyl–4–(3–hydroxyphenyl)piperdine Opioid Antagonists: Applications of the Cis–Thermal Elimination of Carbonates to Alkaloid Synthesis", 1996.

J. E. Zadina, et al., Nature, vol. 1386, pp. 499–502, "A Potent and Selective Endogenous Agonist for the $\mu$–opiate Receptor", Apr. 3, 1997.

D. M. Zimmerman, et al., In Problems of Drug Dependence; Proceedings of the 43$^{rd}$ Annual Scientific Meeting of the Committee on Problems of Drug Dependence Inc., pp. 112–118, "Structural Requirements for Affinity and Intrinsic Activity at the Opiate Receptor Defined in 4–phenylpiperdine and Related Series", 1981.

D. M. Zimmerman, et al., Nature, vol. 275, No. 5678, pp. 332–334, "New Structural Concepts for Narcotic Antagonists Defined in a 4–phenylpiperdine Series", 1978.

D. M. Zimmerman, et al., J. Med. Chem., vol. 31, pp. 555–560, "Synthesis and Analgesic Properties of N–Substituted trans–4A–Aryldecahydroisoquinolines", 1988.

D. M. Zimmerman, et al., Journal of Medicinal Chemistry, vol. 36, No. 20, pp. 2833–2841, "Structure–Activity Relationships of trans–3,4–Dimethyl–4–(3–hydroxyphenyl)piperdine Antagonists for $\mu$–and κ–Opiod Receptors", Oct. 1, 1993.

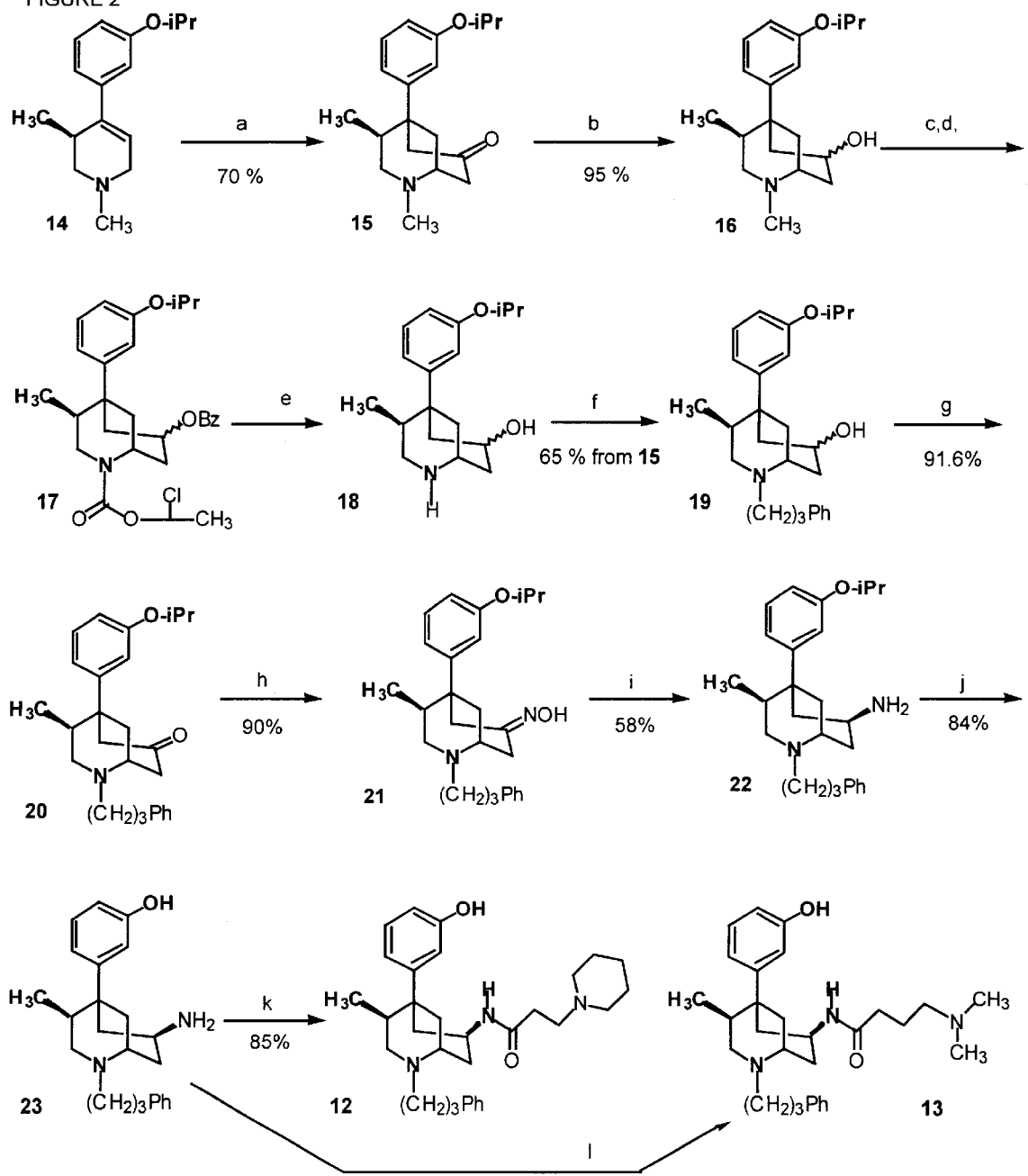

FIGURE 2 a) n-BuLi then ClCH$_2$C(OCH$_2$OCH$_3$)CH$_2$ then 1N HCl, MeOH; b) NaBH$_4$, EtOH; c) Benzoyl chloride, pyridine, CH$_2$Cl$_2$, catalytic 4-N,N-dimethylaminopyridine; d) 1-chloroethylchloroformate, dichloroethane; e) LiOH, H$_2$O, CH$_3$OH; f) NaBH(OAc)$_3$, Ph(CH$_2$)$_2$CHO; g) CO$_2$Cl$_2$, DMSO, Et$_3$N, h) HONH$_2$HCl, EtOH; i) Na, i-PrOH, toluene;j) 48% HBr, glacial HOAc, reflux; k) BOP, Et$_3$N, C$_5$H$_{10}$N(CH$_2$)$_2$CO$_2$H; l) BOP, Et$_3$N, (H$_3$C)$_2$N(CH$_2$)$_3$CO$_2$H.

KAPPA OPIOID RECEPTOR LIGANDS

BACKGROUND OF THE INVENTION

1. Field of the Invention

The present invention relates to compounds that bind with high affinity and/or specificity to kappa opioid receptors.

2. Background of the Invention

The study of compounds exerting their actions via the opioid receptor system has continued for nearly eight decades.[1] Though this has been a broad effort, the fundamental driving force for this endeavor relates to the elimination or reduction of the side-effect profile produced by the most frequently used or abused opiates morphine (1) and heroin (2). The wealth of knowledge accumulated in this time is enormous and includes examples of milestone discoveries commensurate with its breadth from the original concept of an opiate receptor[2] to the more recent cloning of three individual opioid receptor subtypes mu[3–5] delta[6,7] and kappa.[8–10] Belonging to the superfamily of G protein-coupled receptors (GPCR), postulated to possess seven helical transmembrane (7TM) spanning regions, they are now known to be anatomically distributed in both the central and peripheral nervous systems and aside from modulation of pain are intimately involved in a diversity of biological events ranging from of the modulation of immune response[11] to hibernation.[12]

Among the many side effects produced by compounds 1 and 2, addiction, tolerance and respiratory depression are of greatest concern when heroin abuse is considered. Though its use waned in the late 70s, increases in both the purity and availability of this drug have promoted a serious resurgence of illegal use. In the study and treatment of substance abuse, antagonists for the opioid receptors like naltrexone (3) have played a prominent role.[13,14] In recent years, researchers studying the physiological mechanisms underlying addiction have sought antagonists selective for each of the three opioid receptor subtypes mu, delta and kappa. Extensive research efforts along these lines lead to the discovery of several such compounds with examples including cyprodime (mu, 4)[15], naltrindole (delta, 5)[16] and norbinaltorphimine (kappa, 6).[17] Of the three, the kappa receptor has only begrudgingly yielded antagonists and, of the known examples, all stem from modification of the prototype, norbinaltorphimine (nor-BNI, 6) Portoghese in his pioneering work provided not only the second and third generation kappa antagonists 5'-[(N2-butylamidino)methyl]naltrindole (7)[18] and C5'-guanidinylnaltrindole (GNTI, 8)[19] but also convincing evidence that the Glu297 residue in transmembrane helix 6 of the kappa receptor is the principle address site influencing the kappa selectivity found in 6–8. In terms of the message address concept[20] as applied by Portoghese to opioid small-molecules, it is the pendant amine functionality (noted by asterisks in the chart) present in 6–8 that functions as the kappa address element by interacting with the Glu297 residue which is present in the kappa but not in the mu receptor.

In terms of substance abuse treatment, antagonists selective for the kappa receptor have been the least studied primarily due to the limited bio-availability of 6 and its analogs. However, mounting evidence that the endogenous kappa opioid system opposes the actions of mu agonists like 2 suggests that antagonists selective for the kappa receptor could suppress or eliminate the symptoms of withdrawal which arise from an overactive kappa receptor system and thus could promote abstinence and prevent relapse. Therefore, the development of novel kappa antagonists possessing improved pharmacokinetic profiles would be of great value.[21–25]

As is obvious from the examples above, the morphinan substructure of 3 has served as the preeminent template upon which selective antagonists have been constructed. Contrary to these efforts, our work in this field started from the relatively unstudied N-substituted trans-(3,4)-dimethyl-4-(3-hydroxyphenyl)piperidine class of opioid antagonist discovered by Zimmerman et al in the late 70's, (e.g. 9).[26–33] These compounds were novel opioid antagonists because their intrinsic antagonist activity was not mediated by the structure of their N-substituent (i.e. the N-methyl and N-cyclopropylmethyl analogs in the phenylpiperidine series are both pure antagonists). Instead, the antagonist activity in the phenylpiperidine series appears to arise from the 3,4-dimethyl substituents. Early investigations in the 4-phenylpiperidine series suggested that their antagonist activity was mediated through a phenylequatorial mode of binding at opioid receptors. This hypothesis was recently confirmed by the demonstration of potent though non-selective opioid antagonist activity in N-phenethyl-9β-methyl-5-(3-hydroxyphenyl)morphan (10), a conformationally rigid analog of N-phenethyl-trans-3,4-dimethyl-4-(3-hydroxyphenyl)piperidine (9).[34]

SUMMARY OF THE INVENTION

It is an object of the invention to provide compounds which bind to kappa opioid receptors with high affinity.

It is another object of the invention to provide compounds which bind to kappa opioid receptors with high specificity.

It is another object of the invention to provide compounds which bind to kappa opioid receptors with high affinity and specificity.

The objects of the present invention, and others, are accomplished with compounds represented by the formula:

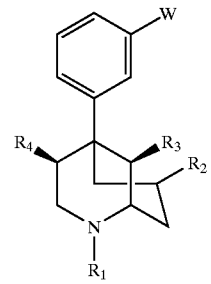

wherein $R_1$ is $C_{2-8}$ alkyl, $C_{3-8}$ alkenyl, $C_{3-8}$ alkynyl, $C_{1-8}$ alkylaryl or one of the following groups:

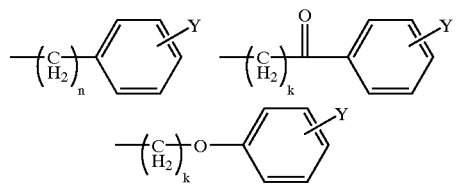

$R_2$ is a member selected from the group consisting of formulae (a)–(pp):

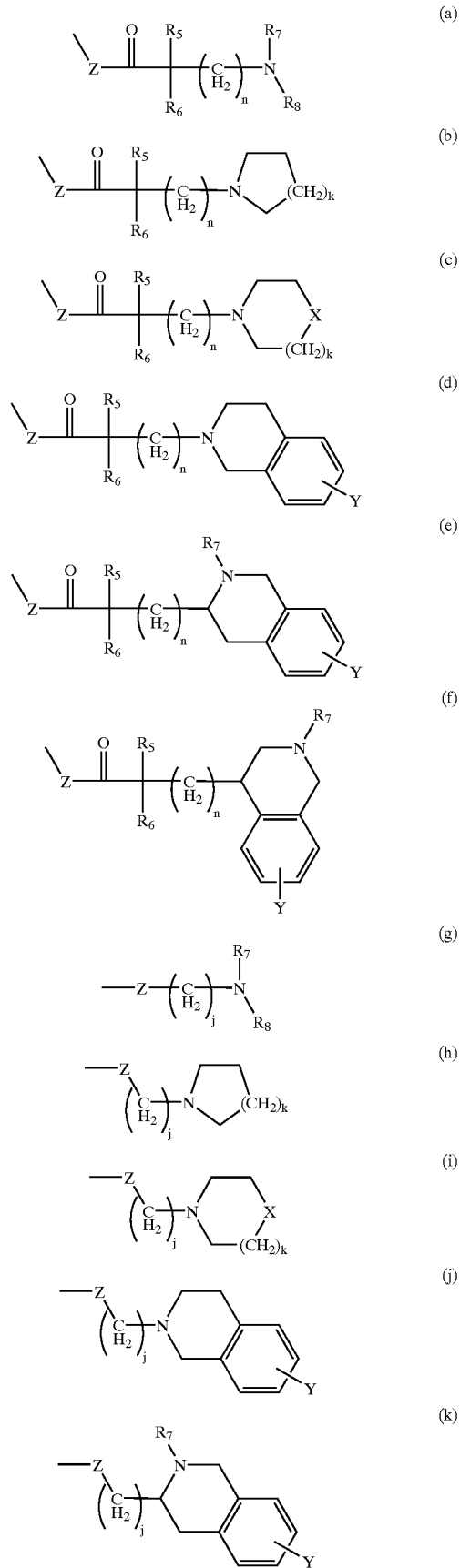
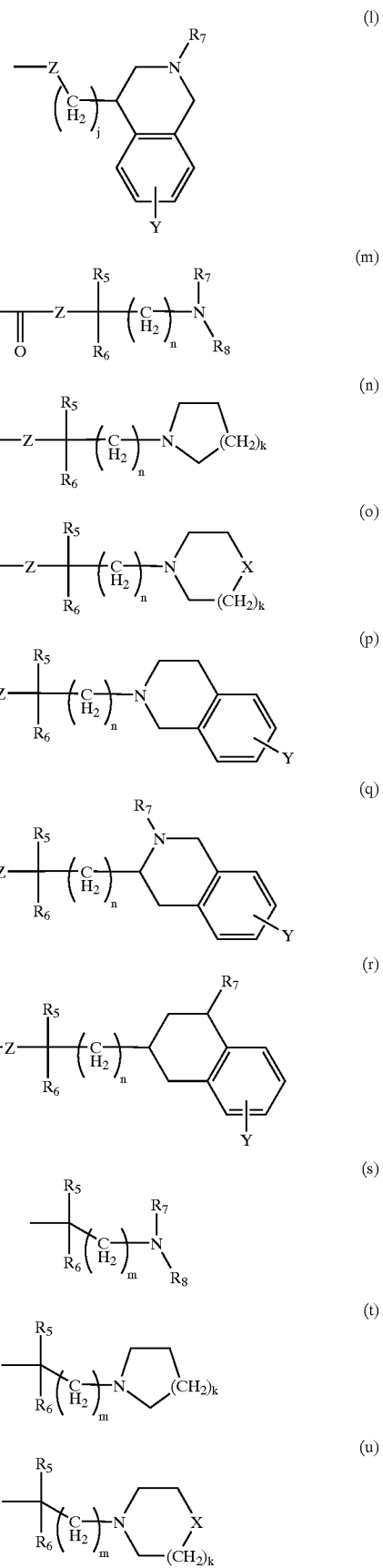

-continued

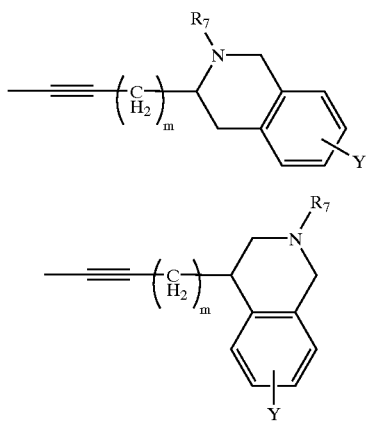

(oo)

(pp)

X is NR, O or S;
Y is OH, OR$_9$, C$_{1-8}$ alkyl, F, Cl, or CF$_3$;
R is hydrogen, C$_{1-8}$ alkyl, C$_{3-8}$ alkenyl, C$_{3-8}$ alkynyl, C$_{1-8}$ alkylaryl, CO$_2$R$_9$
W is a member selected from the group consisting of: H, OH, COOR$_9$; amino, —NR$_3$SO$_2$R$_9$ and —NR$_3$CO$_2$R$_9$;
Z is NR$_3$ or O;
n is 1, 2 or 3;
m is 1, 2, 3 or 4;
j is 2, 3 or 4;
k is 1 or 2;
R$_3$ is hydrogen, C$_{1-8}$ alkyl, C$_{3-8}$ alkenyl, C$_{3-8}$ alkynyl, or C$_{1-8}$ alkylaryl;
R$_4$ is hydrogen, C$_{1-8}$ alkyl, C$_{3-8}$ alkenyl, C$_{3-8}$ alkynyl, or C$_{1-8}$ alkylaryl;
R$_5$ and R$_6$ are each independently, hydrogen, C$_{1-8}$ alkyl, C$_{3-8}$ alkenyl, C$_{3-8}$ alkynyl, or C$_{1-8}$ alkylaryl;
R$_7$ and R$_8$ are each independently, hydrogen, C$_{1-8}$ alkyl, C$_{3-8}$ alkenyl, C$_{3-8}$ alkynyl, or C$_{1-8}$ alkylaryl; and
R$_9$ is C$_{1-8}$ alkyl, C$_{3-8}$ alkenyl, C$_{3-8}$ alkynyl, or C$_{1-8}$ alkylaryl;

and the use of these compounds in pharmaceutical compositions for the treatment of disease states that are ameliorated by binding of the kappa opioid receptor such as heroin or cocaine addictions.

DETAILED DESCRIPTION OF THE INVENTION

A more complete appreciation of the invention and many of the attendant advantages thereof will be readily obtained as the same becomes better understood by reference to the following detailed description when considered in connection with the accompanying drawings, wherein:

FIG. 1: chemical structure of compounds (1)–(13);

FIG. 2: synthesis of illustrative compounds 12 and 13.

DETAILED DESCRIPTION OF THE INVENTION

The present invention provides kappa opioid antagonists that bind to kappa opioid receptors with high affinity and/or specificity. Compounds of the present invention are represented by the formula:

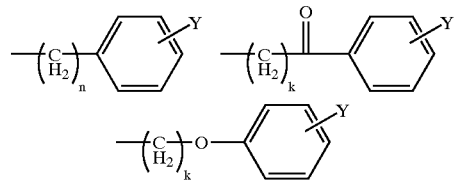

wherein R$_1$ is C$_{2-8}$ alkyl, C$_{3-8}$ alkenyl, C$_{3-8}$ alkynyl, C$_{1-8}$ alkylaryl or one of the following groups:

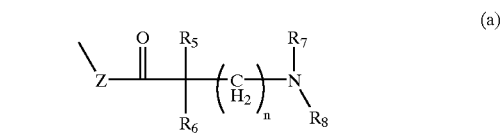

R$_2$ is a member selected from the group consisting of formulae (a)–(pp):

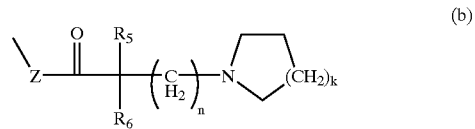

(a)

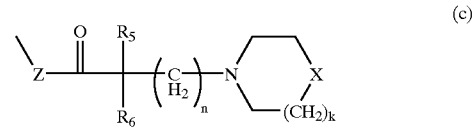

(b)

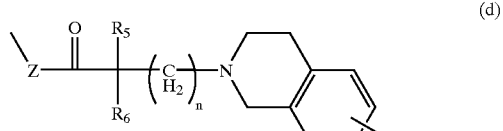

(c)

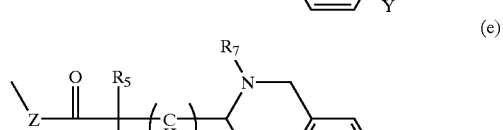

(d)

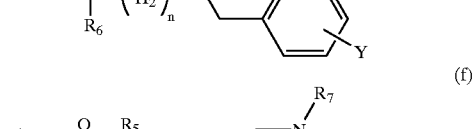

(e)

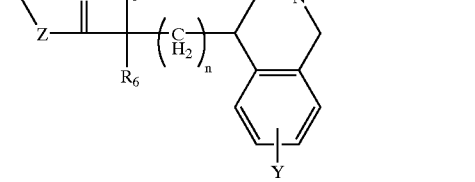

(f)

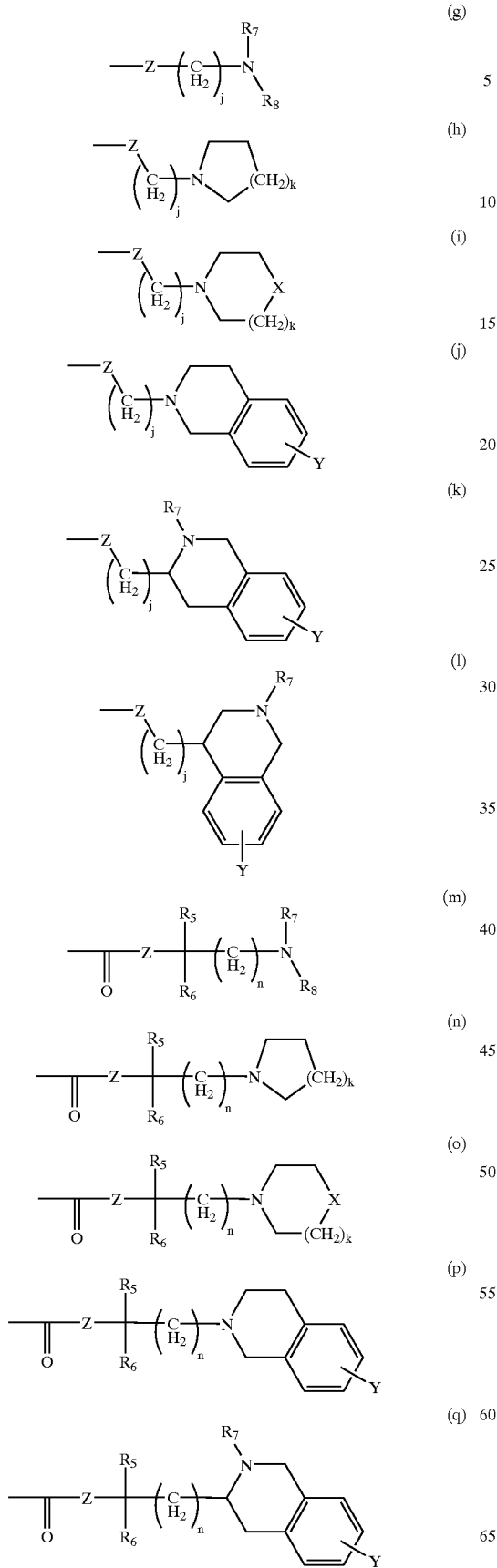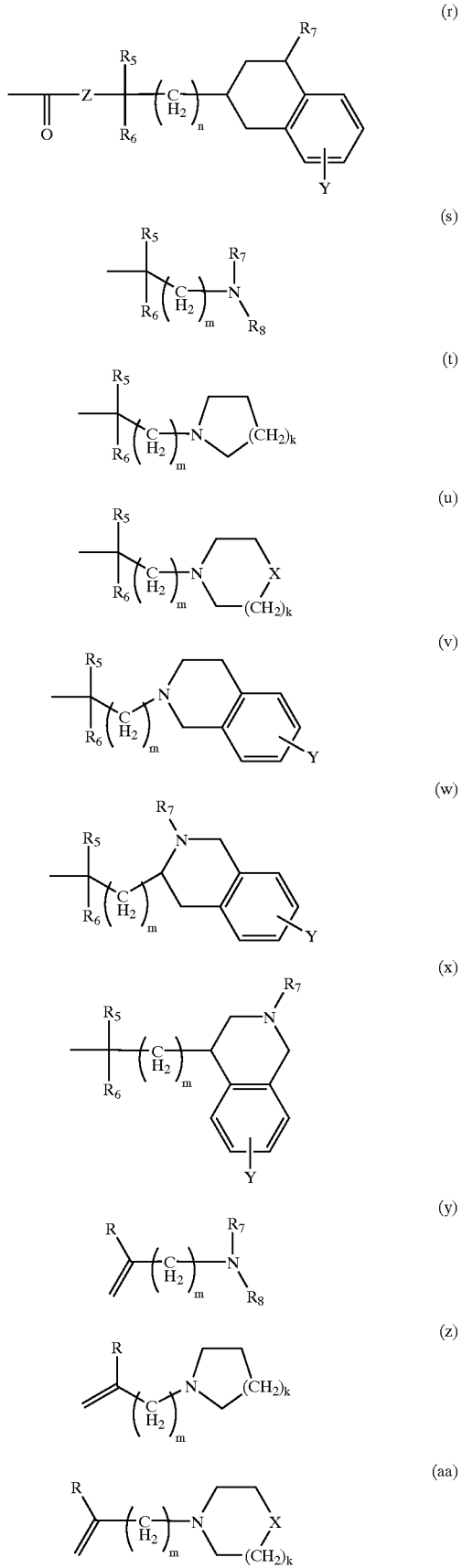

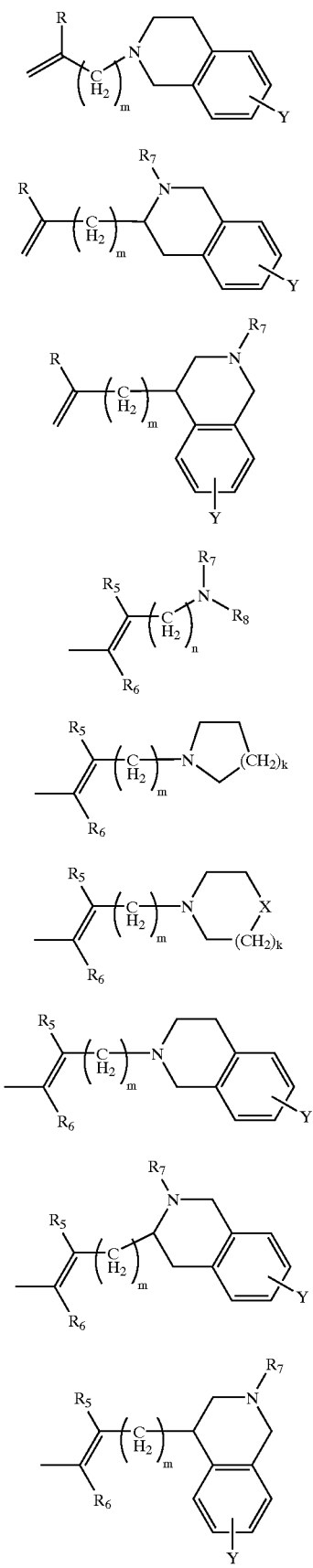

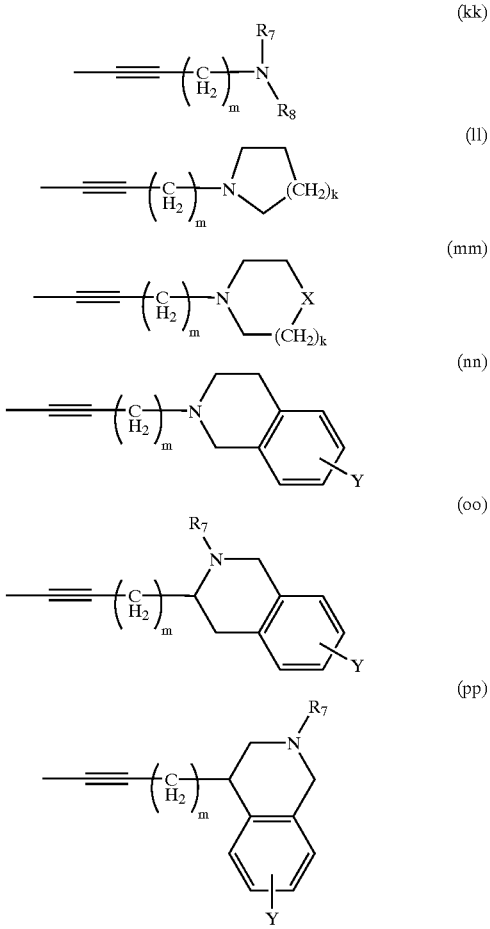

X is NR, O or S;
Y is OH, OR$_9$, C$_{1-8}$ alkyl, F, Cl, or CF$_3$;
R is hydrogen, C$_{1-8}$ alkyl, C$_{3-8}$ alkenyl, C$_{3-8}$ alkynyl, C$_{1-8}$ alkylaryl, CO$_2$R$_9$
W is a member selected from the group consisting of: H, OH, COOR$_9$; amino, —NR$_3$SO$_2$R$_9$ and —NR$_3$CO$_2$R$_9$;
Z is NR$_3$ or O;
n is 1, 2 or 3;
m is 1, 2, 3 or 4;
j is 2, 3 or 4;
k is 1 or 2;
R$_3$ is hydrogen, C$_{1-8}$ alkyl, C$_{3-8}$ alkenyl, C$_{3-8}$ alkynyl, or C$_{1-8}$ alkylaryl;
R$_4$ is hydrogen, C$_{1-8}$ alkyl, C$_{3-8}$ alkenyl, C$_{3-8}$ alkynyl, or C$_{1-8}$ alkylaryl;
R$_5$ and R$_6$ are each independently, hydrogen, C$_{1-8}$ alkyl, C$_{3-8}$ alkenyl, C$_{3-8}$ alkynyl, or C$_{1-8}$ alkylaryl;
R$_7$ and R$_8$ are each independently, hydrogen, C$_{1-8}$ alkyl, C$_{3-8}$ alkenyl, C$_{3-8}$ alkynyl, or C$_{1-8}$ alkylaryl; and
R$_9$ is C$_{1-8}$ alkyl, C$_{3-8}$ alkenyl, C$_{3-8}$ alkynyl, or C$_{1-8}$ alkylaryl;

Of the compounds of the present invention, those that are more preferred are those of the above noted formula wherein:
R$_1$, X, Y, R, W, Z, n, m, j, k, and R$_5$–R$_9$ are the same as noted above;
R$_2$ is a member selected from the group consisting of formulae (a)–(jj)
R$_3$ is hydrogen, or C$_{1-8}$ alkyl; and
R$_4$ is hydrogen, or C$_{1-8}$ alkyl.

Even more preferred are compounds of the above formula, wherein X, Y, W, Z, n, m, j, k, and $R_9$ are as noted above;

$R_1$ is $C_{2-8}$ alkyl, $C_{3-8}$ alkenyl, or a group of the following formulae:

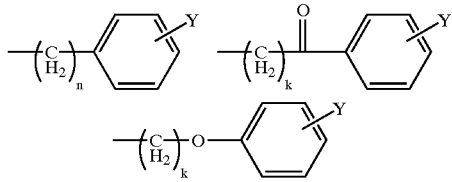

$R_2$ is a member selected from the group consisting of formulae (a)–(dd);

R is hydrogen, $C_{1-8}$ alkyl, $C_{1-8}$ alkylaryl, or $CO_2R_9$;

$R_3$ is hydrogen, or $C_{1-8}$ alkyl;

$R_4$ is hydrogen, or $C_{1-8}$ alkyl;

$R_5$ and $R_6$ are each independently, hydrogen, $C_{1-8}$ alkyl, or $C_{1-8}$ alkylaryl; and $R_7$ and $R_8$ are each independently, hydrogen, $C_{1-8}$ alkyl, or $C_{1-8}$ alkylaryl.

Still more preferred are those compounds wherein X, Y, Z, n, m, j, k, and $R_9$ are the same as noted above;

$R_1$ is $C_{2-8}$ alkyl, $C_{3-8}$ alkenyl, or a group selected from the following formulae:

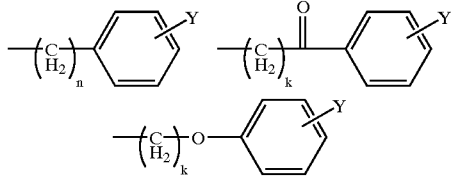

$R_2$ is a member selected from the group consisting of formulae (a)–(r);

R is hydrogen, $C_{1-8}$ alkyl, $C_{1-8}$ alkylaryl, or $CO_2R_9$;

W is OH or $OCOR_9$;

$R_3$ is hydrogen, or $C_{1-4}$ alkyl;

$R_4$ is hydrogen or $C_{1-4}$ alkyl;

$R_5$ and $R_6$ are each independently, hydrogen, or $C_{1-4}$ alkyl; and $R_7$ and $R_8$ are each independently, hydrogen, or $C_{1-4}$ alkyl.

Particularly preferred compounds of the present invention are those of the above noted main formula, wherein X, Y, Z, n, m, j, k, and $R_9$ are as noted above;

$R_1$ is $C_{2-8}$ alkyl, $C_{3-8}$ alkenyl, $C_{1-4}$ alkylaryl or a member selected from the following formulae:

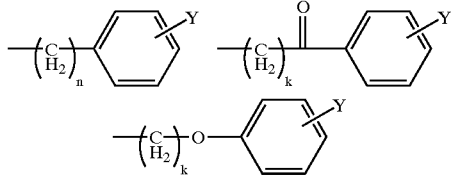

$R_2$ is a member selected from the group consisting of formulae (a)–(i);

R is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$ and $R_6$ are each independently, hydrogen, or $C_{1-4}$ alkyl; and $R_7$ and $R_8$ are each independently, hydrogen, or $C_{1-4}$ alkyl.

Most particularly preferred of the compounds of the present invention are those of the above noted main formula, wherein X, Y, Z, n, m, j, k, and $R_9$ are as noted above;

$R_1$ is $C_{2-8}$ alkyl, $C_{3-8}$ alkenyl, $C_{1-4}$ alkylaryl, or a member selected from the following formulae:

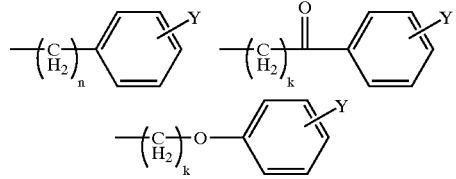

$R_2$ is a member selected from the group consisting of formulae (a)–(f);

R is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$, $R_6$, $R_7$ and $R_8$ are each, independently, H or $C_{1-4}$ alkyl.

A most preferred compound of the present invention is compound 12 and 13 of FIG. 1.

The present inventors have found that attachment of a basic amine functionality (kappa address element) into the bridging ring of the non-selective 4β-methyl analog of compound 10 (11) provides the novel phenylmorphan derivatives (12) and (13), the only phenylmorphan antagonist shown to possess both sub-nanomolar potency and selectivity for the kappa opioid receptor. Additionally, the novel antagonists 12 and 13, unlike 6–8, possess only five heteroatoms in their structures and have molecular weights close to 500 Daltons, a combination of attributes most often associated with small-molecules showing good pharmacokinetic or drug-like properties.

As used throughout this disclosure, the terms "alkyl group" or "alkyl radical" encompass all structural isomers thereof, such as linear, branched and cyclic alkyl groups and moieties. Unless stated otherwise, all alkyl groups described herein may have 1 to 8 carbon atoms, inclusive of all specific values and subranges therebetween, such as 2, 3, 4, 5, 6, or 7 carbon atoms.

As used herein, the term "aralkyl group" refers to an aryl moiety bonded to an alkyl radical. The aryl moiety may have 6 to 20 carbon atoms. The aryl moiety may contain only carbon and hydrogen atoms. Alternatively, the aryl moiety may contain heteroatoms, for example 1, 2, or 3 heteroatoms (e.g., oxygen, nitrogen, and sulfur). A particularly preferred aryl moiety is phenyl-. The alkyl radical of the aralkyl group may be as described above. The alkyl group or moiety and/or the aryl moiety may be substituted. Suitable substituents include halogens (F, Cl, Br and I), alkyl groups (e.g., $C_1$–$C_8$), alkenyl groups (e.g., $C_2$–$C_8$), alkoxy groups (e.g., $C_1$–$C_8$ alkoxy groups), hydroxy, —$CF_3$, —CN, —$NH_2$, —NHR, or —$N(R_a)_2$. The $R_a$ groups are, independently, an alkyl group (such as described above), an aryl group (such as phenyl) or an aralkyl group group (such as benzyl).

Alternatively, the $R_a$ groups may. together, form a cyclic alkyl group. Such a cyclic alkyl group may, preferably, contain 2 to 8 carbon atoms, with 4 or 5 carbon atoms particularly preferred.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more $C_{1-4}$ alkyl group substituents. The aryl moiety of the aryl-$C_{1-8}$ alkyl group is preferably a phenyl group. The phenyl group may be unsubstituted or may be substituted with one or more of the substituents described above. The $C_{1-8}$ alkyl moiety of the aryl-$C_{1-8}$ alkyl group may be unsubstituted or substituted with one or more of the substituents described above or keto, i.e., 2 hydrogens on a carbon atom are replaced by =O. The substituent, when present, is preferably at the beta or gamma carbon atom and/or alpha to the aryl moiety.

The compounds of the present invention are opiates which are preferably antagonists that are selective for the kappa receptor. The $\kappa/\mu$ selectivity may be at least 2:1, but is preferably higher, e.g., at least 5:1, 10:1, 25:1, 50:1, 100:1 or 200:1. The $\kappa/\delta$ selectivity may be at least 2:1, but is preferably higher, e.g., at least 5:1, 10:1, 25:1, 50:1, 100:1, 200:1, 250:1 or 500:1.

The compounds of the present invention may be synthesized, for example, in accordance with the reaction sequence shown in FIG. 2. A specific synthetic sequence for illustrative compounds of the present invention, compounds 12 and 13, is shown in FIG. 2.

The compounds of the present invention may be in the form of a pharmaceutically acceptable salt via protonation of the amine with a suitable acid. The acid may be an inorganic acid or an organic acid. Suitable acids include, for example, hydrochloric, hydroiodic, hydrobromic, sulfuric, phosphoric, citric, fumaric, acetic and formic acids.

The receptor selectivities discussed above are determined based on the binding affinities at the receptors indicated or in functional assays such as the [35S]GTP-γ-S assay.

The compounds of the present invention may be used to bind opioid receptors. Such binding may be accomplished by contacting the receptor with an effective amount of the inventive compound. Of course, such contacting is preferably conducted in a aqueous medium, preferably at physiologically relevant ionic strength, pH, etc.

The inventive compounds may also be used to treat patients having disease states which are ameliorated by binding opioid receptors or in any treatment wherein temporary suppression of the kappa opioid receptor system is desired. These compounds are also useful where enhancement of response to kappa agonists is beneficial. Such diseases states include opiate addiction (such as heroin addiction), or cocaine addiction. The compounds of the present invention may also be used as cytostatic agents, as antimigraine agents, as immunomodulators, as immunosuppressives, as antiarthritic agents, as antiallergic agents, as virucides, to treat diarrhea, as antipsychotics, as antischizophrenics, as antidepressants, as uropathic agents, as antitussives, as antiaddictive agents, as anti-smoking agents, to treat alcoholism, as hypotensive agents, to treat and/or prevent paralysis resulting from traumatic ischemia, general neuroprotection against ischemic trauma, as adjuncts to nerve growth factor treatment of hyperalgesia and nerve grafts, as anti-diuretics, as stimulants, as anti-convulsants, or to treat obesity. Additionally, the present compounds can be used in the treatment of Parkinson's disease as an adjunct to L-dopa for treatment of dyskinesia associated with the L-dopa treatment. They may also be used with kappa agonists as analgesics, or for any condition requiring suppresion of the kappa receptor system.

The compounds may be administered in an effective amount by any of the conventional techniques wellestablished in the medical field. For example, the compounds may be administered orally, intraveneously, or intramuscularly. When so administered, the inventive compounds may be combined with any of the well-known pharmaceutical carriers and additives that are customarily used in such pharmaceutical compositions. For a discussion of dosing forms, carriers, additives, pharmacodynamics, etc., see Kirk-Othmer Encyclopedia of Chemical Technology, Fourth Edition, Vol. 18, 1996, pp. 480–590. incorporated herein by reference. The patient is preferably a mammal, with human patients especially preferred. Effective amounts are readily determined by those of ordinary skill in the art. Studies by the present inventors show no toxicity and no lethality for the present compounds at amounts up to 300 mg/kg in mice.

The compounds of the present invention can be administered as a single dosage per day, or as multiple dosages per day. When administered as multiple dosages, the dosages can be equal doses or doses of varying amount, based upon the time between the doses (i.e. when there will be a longer time between doses, such as overnight while sleeping, the dose administered will be higher to allow the compound to be present in the bloodstream of the patient for the longer period of time at effective levels). Preferably, the compound and compositions containing the compound are administered as a single dose or from 2–4 equal doses per day.

Suitable compositions containing the present compounds further comprise a physiologically acceptable carrier, such as water or conventional pharmaceutical solid carriers, and if desired, one or more buffers and other excipients.

EXAMPLES

Having generally described this invention, a further understanding can be obtained by reference to certain specific examples which are provided herein for purposes of illustration only and are not intended to be limiting unless otherwise specified.

Chemistry

The synthesis of 12 and 13 shown in FIG. 2 began with optically pure (S)-1,2,3,6-tetrahydro-1,3-dimethyl-4-[3-(1-methylethoxy)phenyl]pyridine[14,35] by treating it with n-BuLi to form the metalloenamine which was then cannulated into a solution of 2-(chloromethyl)-3,5-dioxohex-1-ene (Okahara's reagent) in tetrahydrofuran (THF).[36–38] The intermediate thus formed was not isolated, but allowed to stir in methanol and 2N HCl to give (−)-N-(1R,4S,5S)-5-[3-(1-methylethoxy)phenyl]-2,4-di-methyl-2-azabicyclo [3.3.1]non-7-one 15 in 70% yield.[39] As previously discovered, this transformation occurs in a highly stereospecific fashion with the methyl group directing approach of the alkylating agent from the opposite face of the piperidine ring. Since the subsequent cyclization of the alkylated intermediate to give 15 can occur only on the same face of the piperidine ring, the directing effect of the methyl group in 14 is responsible for the stereospecific placement of two stereocenters (C1 and C5) and thus only 15 was isolated from the reaction mixture.

Since antagonists of the phenylmorphan series like 10 are known to be far more potent with N-substituents larger than methyl (i.e. phenylethyl or phenylpropyl),[34] replacement of the methyl N-substituent in 15 became necessary. Normally this is accomplished by treatment with a chloroformate reagent such as 1-chloroethyl chloroformate (ACE-Cl) to give an intermediate carbamate which can then be hydrolysed to expose the secondary amine. However, repeated attempts with a variety of chloroformate reagents failed to produce the desired result. Apparently, the energy of the lone pair of electrons on the nitrogen atom in 15 is considerably different from that found in typical tertiary amines presumably due to interaction with the carbonyl group. This notion is supported by the fact that reduction of the carbonyl eliminated the errant behavior. Conversion of 15 to 19 was ultimately accomplished in 65% overall yield without isolation of intermediates by reducing the carbonyl in 15 with $NaBH_4$ to give 16, followed by protection of the hydroxyl group as the benzoate ester, and treatment of the resulting ester with ACE-Cl to give 17. Hydrolysis of both the newly formed carbamate and benzoate groups was then performed using LiOH in aqueous refluxing methanol to give the secondary amine 18 which was then converted to the phenylpropyl derivative 19 by treatment with hydrocinnamaldehyde and $NaBH(OAc)_3$.[40] Swern oxidation of 19 followed by conversion of the carbonyl to the oxime with hydroxylamine hydrochloride and finally reduction of the oxime using sodium and isopropanol gave 22 in 54% yield from 19. This reaction sequence has been shown to produce only the 7β-epimer in phenylmorphan systems lacking the 4β-methyl group.41 Inline with these observations, only the 7β-epimer was observed in the present example. Removal of the isopropyl group in 22 using HBr in acetic acid followed by coupling with 1-piperidinepropionic acid or 4-dimethylaminobutyric acid using benzotriazol-1-yl-oxy-tris-(dimethylamino)phosphonium hexafluorophosphate (BOP, Castro's reagent) gave the desired compounds 12 and 13, respectively.

Biological Activity

The binding affinities of 12, 13, the reference compound 10 and the standard kappa antagonist 6 for the mu, delta, and kappa opioid receptors were determined using competitive binding assays following previously reported procedures. Table 1.[42] Measures of antagonism were obtained by monitoring the test compounds ability to inhibit stimulation of [$^{35}S$]GTP-γ-S binding produced by the selective agonists (D-Ala$^2$,MePhe$^4$,Gly-ol$^5$)enkephalin (DAMGO, mu receptor), (+)-4-[((αR)-α-(2S,5R)-4-allyl-2,5-dimethyl-1-piperazinyl)-3-methoxybenzyl]-N,N-diethylbenzamide (SNC-80, delta) and 5α,7α,8β-(-)-N-methyl-N-[7-(1-pyrrolidinyl)-1-oxaspiro[4,5]dec-8-yl]benzeneacetamide (U69.593, kappa) in guinea pig caudate (Table 2) and in human receptor clones, Table 3.

Results

Inspection of the binding data for the phenylmorphan derivative 10 in Table 1 reveals that it is not selective for any opioid receptor and displays its highest affinity for mu ($K_i$=3.11 nM) receptor. This is not unexpected since this binding profile is typical of that seen in many phenylpiperidine antagonists and as was mentioned earlier, the phenylmorphan derivative 10 is in essence a rigid analog of the phenylpiperidine antagonist 9.[32,34] The data for compound 12 however, is quite different from that found for 10. In this case, the affinity for the mu receptor is some 50-fold lower ($K_i$=147 nM) and the highest affinity is now observed to be for the kappa receptor with a $K_i$=4.3 nM. In binding to the delta receptor, compound 10 shows significantly greater affinity relative to 12. Indeed, within the testing parameters, compound 12 shows no affinity for this receptor subtype.

Compound 13 compares favorably with the data obtained for 12 in that it now is selective for the kappa over the mu or delta receptors but unlike 12, it shows slightly less affinity for the kappa receptor and slightly greater affinity for the mu receptor. In comparison to the prototypical kappa antagonist nor-BNI (6), it is clear that 12 is selective for the kappa receptor with a mu/kappa selectivity ratio approximately half of that found for 6. In the delta receptor assay compound 12 shows a much improved delta/kappa selectivity profile of >790-fold relative to the 79-fold ratio observed for nor-BNI (6). Taken together, the data from the binding assay indicates that the novel antagonist (12) is not only selective for the kappa opioid receptor over the mu and delta subtypes, unlike typical phenylmorphan-based antagonists (10), but also shows an improved delta/kappa selectivity profile compared with the standard kappa antagonist nor-BNI (6).

The data obtained from compounds 6, 10 and 12 for inhibition of agonist stimulated GTP-γ-S binding as measured in guinea pig caudate membranes is given in Table 2. Inspection of this information indicates that the trends found in antagonist potency closely parallel those found in the binding assay. Specifically, the non-selective phenylmorphan antagonist 10 retains the mu receptor as its principle site of action, but also shows significant antagonism for both the delta and kappa receptors. However, compared to the $K_i$ found in the binding assay for 10, its' $K_i$ for the mu receptor in the functional assay, is improved by an order of magnitude. Similar parallels in behavior were found for the novel phenylmorphan antagonist 12. For example, 12 is observed to retain the kappa receptor as its' principle site of action, but as was the case for 10, the $K_i$ for the kappa receptor in the functional assay, is improved by an order of magnitude. In terms of selectivity, the behavior for compound 12 between the two assays is observed to diverge. Specifically, the mu versus kappa selectivity of compound 12 is twice as great in the functional assay relative to the binding assay. Inspection of the data reveals that the primary reason for the observed doubling in selectivity is the 10-fold increase in $K_I$ found for 12 in the kappa receptor functional assay. The mu receptor $K_1$ also increases but by only 4-fold and thus the increase in kappa potency drives the selectivity ratio higher in favor of the kappa receptor. The data for the standard antagonist 6 follows the trends observed above especially in the enhancement of kappa selectivity resulting from a significant increase in $K_I$ in the functional assay. In comparison with 6, the phenylmorphan derivative 12 is about 6-fold less selective than the standard (6) for the mu versus the kappa receptor, but as before, compound 12 retains a superior delta versus kappa selectivity due primarily to the inability of 12 to interact measurably with the delta receptor. Overall, the data from the functional assay demonstrates that the novel phenylmorphan-based antagonist 12 is both potent and selective for the kappa opioid receptor.

In a similar assay for antagonist potency using cloned human opioid receptors instead of guinea pig membranes, the novel antagonist 12 was found to retain both kappa opioid receptor selectivity and sub-nanomolar potency as did the standard antagonist nor-BNI (6). In this assay the kappa selectivity is slightly diminished relative to the guinea pig preparation with mu/kappa selectivity ratios of 64 and 70 respectively. Nevertheless, the delta/ratio remains high and is, as before, driven by an apparent lack of affinity of 12 for the delta opioid receptor. Taken together with the observations made in guinea pig caudate, the data from the cloned human receptors confirms that (−)-N-[(1R,4S,5S, 7R)-5-(3-hydroxy)phenyl-4-methyl-2-(3-phenylpropyl)-2-azabicyclo[3.3.1]non-7-yl]-3-(1-piperidinyl)propanamide (12) is a highly selective and potent antagonist for the kappa opioid receptor.

TABLE 1

Radioligand Binding Data for Test Compounds and nor-BNI in Mu, Delta, and Kappa Opioid Receptor Assays

| Compound | $K_i$ (nM ± SD) | | | | |
|---|---|---|---|---|---|
| | [$^3$H]DAMGO[a] | [$^3$H]DADLE[b] | [$^3$H]U69,593[c] | | |
| 6, nor-BNI | 65.0 ± 5.6 | 86 ± 7.2 | 1.09 ± 0.14 | 60 | 79 |
| 10 | 3.11 ± 0.21 | 272 ± 30 | 14.5 ± 0.99 | 0.21 | 19 |
| 12 | 147 ± 9.8 | >3400 | 4.3 ± 0.7 | 34 | >790 |
| 13 | 57 ± 5.4 | 1457 ± 113 | 11.9 ± 0.65 | 5 | 122 |

[a][$^3$H]DAMGO [(D-Ala$^2$,MePhe$^4$,Gly-ol$^5$)enkephalin]. Tritiated ligand selective for mu opioid receptor.
[b][$^3$H]DADLE [(D-Ala$^2$,D-Leu$^5$)enkephalin]. Tritiated ligand selective for delta opioid receptor.
[c][$^3$H]U69,593 {[$^3$H](5, 7, 8)-(−)-N-methyl-N-[7-(1-pyrrolidinyl)-1-oxaspiro[4,5]dec-8-yl]benzeneacetamide}. Tritiated ligand selective for kappa opioid receptor.

TABLE 2

Inhibition by Antagonists of [$^{35}$S]GTPγS Binding in Guinea Pig Caudate Stimulated by DAMGO (mu), SNC-80 (delta) and U69,593 (kappa) Selective Opioid Agonists.

| Compound | Apparent Functional $K_i$ (nM ± SD) | | | | |
|---|---|---|---|---|---|
| | DAMGO[a] | SNC-80[b] | U69,593[c] | μ/κ | δ/κ |
| 6, nor-BNI | 16.75 ± 1.47 | 86 ± 7.2 | 1.09 ± 0.14 | 60 | 79 |
| 10 | 0.338 ± 0.028 | 12.6 ± 1.01 | 1.34 ± 0.084 | 0.25 | 9.4 |
| 12 | 33.6 ± 10.4 | >300 nM | 0.48 ± 0.06 | 70 | >625 |

[a]DAMGO [(D-Ala$^2$,MePhe$^4$,Gly-ol$^5$)enkephalin] is an agonist selective for mu opioid receptor. The apparent functional $K_i$ is the concentration of each compound required to produce a 50% attenuation of DAMGO (10 μm)-stimulated [$^{35}$S]GTP-γ-S binding.
[b]SNC-80 ([(+)-4-[(αR)-α-(2S,5R)-4-allyl-2,5-dimethyl-1-piperazinyl]-3-methoxybenzyl]-N,N-diethylbenzamide) is an agonist selective for delta opioid receptor. The apparent functional $K_i$ is the concentration of each compound required to produce a 50% attenuation of SNC80 (10 μM)-stimulated [$^{35}$S]GTP-γ-S binding.
[c]U69,593 [(5α,7α,8β)-(−)-N-methyl-N-[7-(1-pyrrolidinyl)-1-oxaspiro[4.5]dec-8-yl]benzeneacetamide]. Agonist selective for kappa opioid receptor. The apparent functional concentration of each compound required to produce a 50% attenuation of U69,593 (10 μM)-stimulated [$^{35}$S]GTP-γ-S binding.

TABLE 3

Inhibition by Antagonists 6 and 12 of [$^{35}$S]GTPγS Binding in Cloned Human Opioid Receptors Stimulated by DAMGO (mu), SNC-80 (delta) and U69,593 (kappa) Selective Opioid Agonists.

| Compound | Apparent Functional $K_i$ (nM ± SD) | | | | |
|---|---|---|---|---|---|
| | DAMGO[a] | SNC-80[b] | U69,593[c] | μ/κ | δ/κ |
| 6,nor-BNI | 15.8 ± 5.7 | 12.1 ± 3.1 | 0.07 ± 0.03 | 225 | 172 |
| 12 | 35.8 ± 6.8 | >100 | 0.56 ± 0.08 | 64 | >178 |

[a]DAMGO [(D-Ala$^2$,MePhe$^4$,Gly-ol$^5$)enkephalin] is an agonist selective for mu opioid receptor. The apparent functional $K_i$ is the concentration of each compound required to produce a 50% attenuation of DAMGO (10 μM)-stimulated [$^{35}$S]GTP-γ-S binding.
[b]SNC-80 ([(+)-4-[(αR)-α-(2S,5R)-4-allyl-2,5-dimethyl-1-piperazinyl]-3-methoxybenzyl]-N,N-diethylbenzamide) is an agonist selective for delta opioid receptor. The apparent functional $K_i$ is the concentration of each compound required to produce a 50% attenuation of SNC80 (10 μm)-stimulated [$^{35}$S]GTP-γ-S binding. considering
[c]U69,593 [(5α,7α,8β)-(−)-N-methyl-N-[7-(1-pyrrolidinyl)-1-oxaspiro[4.5]dec-8-yl]benzeneacetamide]. Agonist selective for kappa opioid receptor. The apparent functional concentration of each compound required to produce a 50% attenuation of U69,593 (10 μM)-stimulated [$^{35}$S]GTP-γ-S binding.

Experimental Section

Melting points were determined on a Thomas-Hoover capillary tube apparatus and are not corrected. Elemental analyses were obtained by Atlantic Microlabs, Inc. and are within ±0.4% of the calculated values. All optical rotations were determined at the sodium D line using a Rudolph Research Autopol III polarimeter (1-dm cell). $^1$H-NMR were determined on a Bruker WM-250 spectrometer using tetramethylsilane as an internal standard. Silica gel 60 (230–400 mesh) was used for all column chromatography. All reactions were followed by thin-layer chromatography using Whatman silica gel 60 TLC plates and were visualized by UV or by charring using 5% phosphomolybdic acid in ethanol. All solvents were reagent grade. Tetrahydrofuran and diethyl ether were dried over sodium benzophenone ketyl and distilled prior to use.

The [$^3$H]DAMGO, DAMGO, and [3H][D-Ala$^2$,D-Leu$^5$] enkephalin were obtained via the Research Technology Branch, NIDA, and were prepared by Multiple Peptide Systems (San Diego, Calif.). The [$^3$H]U69.593 and [$^{35}$SIGTP-γ-S (SA=1250 Ci/mmol) were obtained from DuPont New England Nuclear (Boston, Mass.). U69.593 was obtained from Research Biochemicals International (Natick, Mass.). Levallorphan was a generous gift from Kenner Rice, Ph.D., NIDDK, NIH (Bethesda, Md.). GTP-γ-S and GDP were obtained from Sigma Chemical Company (St. Louis, Mo.). The sources of other reagents are published. (CAUTION: Read reference 35 and references cited therein for information on N-methyl-4-phenyl-1,2,3,6-tetrahydropyridine. MPTP and its derivatives).

(−)-(1R,4S,5S)-5-[3-(1-methylethoxy)phenyl]-2,4-di-methyl-2-azabicyclo[3.3.1]nonan-7-one (15)

To a solution of (S)-1,2,3,6-tetrahydro-1,3-dimethyl-4-[3-(1-methylethoxy)phenyl]pyridine (14) (1 eq) dissolved in THF (20 mL/g) and cooled to −10° C. was added n-butyl lithium (1.6M in hexanes) slowly until a red color is maintained followed by an addition of 1.1 eq. This material is stirred for 1 h at 10° C. and then cannulated quickly into a solution of Okahara's reagent (distilled to high purity) in THF (15 mL/g, 1.1 eq) at −78° C. followed by stirring for 2 h. The temperature should be kept below −30° C. during cannulation. This material is then poured into 2N HCl and extracted twice with ethyl ether. The aqueous layer is allowed to stand for 15 min followed by addition of 50% NAOH to pH 14 and extraction (3×) with ethyl ether. The ether is then washed (1N NaOH, H$_2$O) and the solvent removed under vacuum. The resulting residue of product and water is dissolved in MeOH (30 mL/g) and nitrogen is bubbled through the solution for 5 min. To this is added concentrated HCl (2 mL/g), and the mixture is allowed to stand at room temperature until the reaction is complete as indicated by TLC (TLC condition: SiO$_2$; elution with 50% (80% CHCl$_3$:18% CH$_3$OH:2% NH$_4$OH) in CHCl$_3$. Detection: 5% phosphomolybdic acid in ethanol. To this mixture was added 50% NaOH to adjust the pH to ~10 and the methanol is removed under aspirator vacuum. The aqueous residue is then extracted several times with 3:1 (methylene chloride:THF). The organic extracts are combined and washed twice with water and once with brine, dried over sodium sulfate and evaporated to an oil. This material was purified by flash chromatography on silica gel using 25–50% (80% CHCl$_3$:18% CH$_3$OH:2% NH$_4$OH) in CHCl$_3$ to give 15 in 70% yield from 14. $^1$H NMR 7.24 (t,1,J=7.5 Hz), 6.77 (m, 3), 4.55 (m, 1), 3.49 (s, 1), 2.91 (dd,2,J=17 Hz and 16.5 Hz), 2.60 (m, 2), 2.35 (m, 5), 2.05 (m, 3), 1.35 (m, 6), 0.78 (d,3,J=6.8 Hz).

(−)-(1R,4S,5S)-5-[3-(1-methylethoxy)phenyl]-2,4-di-methyl-2-azabicyclo[3.3.1]nonan-7-ol (16)

To a solution of 15 (1 eq) dissolved in absolute ethanol (7 mL/g of 15) was added solid sodium borohydride slowly over 10 minutes. This mixture was allowed to stir at room temperature for 24 hours after which time the ethanol was removed under aspirator vacuum and the residue carefully dissolved in 0.5N HCl (6 mL/g of 15). This solution was washed twice with ether (3 mL/g of 15 for each wash) and then the aqueous solution is made basic with 50% NaOH solution (pH=14) and the ether layers discarded. This solution was then saturated with sodium chloride and extracted five times with 3:1, methylene chloride:THF, (3 mL/g of 15 for each extraction) and the combined organic layers were dried over magnesium sulfate and the solvent removed under aspirator vacuum to provide 16 as a yellow oil in 95% yield from 15 as a mixture of 7-hydroxy diastereomers. This material is used in the next step without purification. $^1$H NMR (CDCl$_3$): δ0.46–0.48(d, J=6.90 Hz, 3H), 1.32–1.34 (d, J=6.02 Hz, 6H), 1.47–1.58(m, 2H), 1.87–1.93(dd, J=14.16, 5.09 Hz, 2H), 2.27–2.47 (m, 8H), 2.69–2.75 (dd, J=11.64, 5.26 Hz, 1H), 3.09 (br s, 1H), 4.02–4.05 (t, J=4.83 Hz, 1H), 4.47–4.59 (septet, J=6.07 Hz, 1H)5.30 (br s, 1H), 6.68–6.81 (m, 3H), 7.7.16–7.62 (in, 1H).

(−)-(1R,4S,5S, 7R)-5-[3-(1-methylethoxy)phenyl]-4-methyl-2-(3-phenylpropyl)-2-azabicyclo-[3.3.2]nonan-7-ol (19)

To a solution of 16 (1 eq) in anhydrous methylene chloride (35 mL/g of 16) at room temperature, was added triethylamine (1.1 eq), a small amount of N,N-dimethylaminopyridine, pyridine (0.3 eq) and benzoyl chloride (1.6 eq) and the resulting mixture was stirred over night under a nitrogen atmosphere. Following this, the mixture was washed 2 times with 10% NaOH, 1 time with water and then dried over sodium sulfate and the solvent removed under reduced pressure. The resulting oil was not purified but carried directly to the next step. $^1$H NMR (CDCl$_3$): δ8.18 (d), 8.02 (d), 7.56 (d), 7.46 (d), 7.20 (t), 6.75-6.69 (m), 5.32-5.28 (m), 4.56-4.52 (quintet), 3.65-3.50 (m), 3.30-3.15 (dd), 3.00 (s), 2.78-2.75 (q), 2.49(s), 2.44 (s), 2.43-2.25 (m), 2.30(s), 2.25-1.85 (m), 1.34-1.32 (d), 1.17-1.12 (t), 0.76-0.74 (d). To a solution of this oil (1 eq) in anhydrous 1,2-dichloroethane (20 mL/g of 16) at reflux was added 1-chloroethyl chloroformate (1.1 eq) dropwise. The resulting solution was heated under reflux for 2.5 hours and then cooled to room temperature. This mixture was then washed 1 time with saturated bicarbonate solution, 1 time with water and then the organic layer was evaporated and the resulting oil dissolved immediately in 1:1 methanol:water. To this was added LiOH (1 g/g of 16) and then heated to reflux until the reaction was complete as judged by TLC (~2 hours). After cooling to room temperature, the methanol was removed under aspirator vacuum and the remaining aqueous solution saturated with sodium chloride. This was then extracted with butanol (10 times) and the combined butanol extracts washed once with water. Removal of the solvent provided slightly impure 18 which was not purified, but carried directly to the next step. $^1$H NMR (CDCl$_3$): δ0.48-0.65 (m, 3H), 1.32-1.34 (d, 6H), 1.54-1.72 (m, 2H), 1.97–2.12(m, 4H), 2.58–2.64 (m, 1H), 3.45–3.59 (m, 3H), 3.91–4.02 (m, 1H), 4.47–4.68 (m, 1H), 6.68–6.78 (m, 3H), 7.17–7.35 (t, 1H). To a solution of 18 (1 eq) in anhydrous 1,2-dichloroethane (40 mL/g of 18) was added hydrocinnamaldehyde (freshly opened, 1.2 eq) and NaBH(OAc)$_3$ (1.2 eq) and the resulting mixture stirred for 24 hours. After this time, the resulting mixture was washed with 1N NAOH and the aqueous layer back extracted with chloroform. The combined organic layers were dried over sodium sulfate and the solvent was removed at reduced pressure to give crude 19 as a mixture of diastereomers. This material was purified by flash chromatography on silica gel to give 19 as a yellow oil in 65% yield from 16. $^1$H NMR (CDCl$_3$): δ0.43–0.45 (d, J=6.82 Hz, 3H), 1.31–1.33 (d, J=6.03 Hz, 6H), 1.40–1.53 (m, 2H), 1.81–1.88 (m, 4–5 H), 2.27–270 (m, 10H), 3.14 (s, 1H), 4.06 (s, 1H), 4.51–4.55 (m, 1H), 6.08 (br s, 1H), 6.68–6.89 (m, 3H), 7.15–7.54 (m, 6H).

(−)-[(1R,4S,5S,7R)-5-[3-(1-methylethoxy)phenyl]-4-methyl-2-(3-phenylpropyl)-2-azabicyclo-[3.3.1]nonan-7-one (20)

Dimethyl sulfoxide (6.6 eq) in dry CH$_2$Cl$_2$ (3 mL/g of 19) was added dropwise over 20 min to a solution of 2 M oxalyl chloride (3 eq) in CH$_2$Cl$_2$ at −78° C. The reaction mixture was allowed to warm to −20° C. Maintaining a temperature of −20° C., 19 (1 eq) in CH$_2$Cl$_2$ (4 mL/g of 19) was added dropwise over 15 min. to the reaction mixture. The reaction was stirred for an additional 30 min. and then quenched with the careful addition of triethylamine (8 eq). The reaction mixture was allowed to warm to room temperature, washed with saturated NaHCO$_3$, and the organic layer was collected, dried (Na$_2$SO$_4$) and the solvent removed under reduced pressure. The crude product was purified by flash chromatography (5%-10% (80% CHCl$_3$:18% CH$_3$OH:2% NH$_4$OH) in CH$_2$Cl$_2$) to afford 20 (91%) as yellow oil. $^1$H-NMR (CDCl$_3$) δ7.23 (m, 6H), 6.77 (m, 3H), 4.54 (sept., 1H, J=6.1 Hz), 3.47 (br., 1H), 2.83 (m, 2H), 2.68–2.52 (m, 5H), 2.43 (t, 2H, J=6.9 Hz), 2.09-1.95 (m, 3H), 1.74 (m, 3H), 1.33 (d, 6H, J=6.0 Hz), 0.79 (d, 3H, J=6.8 Hz).

(−)-[(1R,4S,5S,7R)-5-[3-(1-methylethoxy)phenyl]-4-methyl-2-(3-phenylpropyl)-2-azabicyclo-[3.3.1]nonan-7-one Oxime (21)

Compound 20 (1 eq) and hydroxylamine hydrochloride (5 eq) in EtOH (absolute. 17 mL/g of 20) were heated under reflux for 3 h. The reaction mixture was allowed to cool to room temperature and the ethanol was removed under reduced pressure. The oil thus obtained was dissolved in 2 M NaOH (17 mL/g of 20) and the product extracted with 3:1 CH$_2$Cl$_2$/THF (4×10 mL/g of 20). The organic layers were collected, dried (Na$_2$SO$_4$) and the solvent was removed under reduced pressure. The product obtained was purified by flash chromatography (5%-10% (80% CHCl$_3$:18% CH$_3$OH:2% NH4OH) in CH$_2$Cl$_2$) to afford 21 (90%) as yellow oil. $^1$H-NMR (CDCl$_3$) δ10.09 (br., 1H), 7.26-7.13 (m, 6H), 6.88–6.72 (m, 3H), 4.54 (m, 1H), 3.63 (d, 1H, J=17 Hz), 3.29 (br., 1H), 2.94-2.85 (m, 2H), 2.69-2.41 (m, 5H), 2.29 (d, 1H, J=15.9 Hz), 2.04-1.65 (m, 6H), 1.33 (d, 6H, J=6.0 Hz), 0.76 (d, 3H, J=6.9 Hz).

(−)-1(1R,4S,5S,7R)-5-[3-(1-methylethoxy)phenyl]-4-methyl-2-(3-phenylpropyl)-2-azabicyclo-[3.3.1]nonan-7-amine (22)

Compound 21 (1 eq) (5.51 g, 13.1 mmole) in a minimum of dry isopropanol was added dropwise over 1 h. to a refluxing mixture of dry toluene (35 mL/g of 21) and sodium (150 eq). After complete addition of oxime, two portions of isopropanol (23 mL/g of 21) was added dropwise over 30 min. The reaction mixture was heated to reflux until all the sodium was consumed. The reaction mixture was allowed to cool to 50° C. and then quenched with by careful addition of water (135 mL/g of 21). The toluene layer was separated and the aqueous layer was extracted with CHCl₃ (4×90 mL/g of 21). The organic layers were combined, dried (Na₂SO₄) and the solvent was removed under reduced pressure. The product was purified by flash chromatography (25%50% (80% CHCl₃:18% CH₃OH:2% NH₄OH) in CHCl₃) to afford starting material 21 (18% recovered) and 22 (58%) as yellow oil. ¹H-NMR (CDCl₃) δ7.28-7.15 (m, 6H), 6.76-6.68 (m, 3H), 4.52 (sept., 1H, J=6.1 Hz), 3.51 (m, 1H), 3.13 (m, 1H), 2.82 (m, 1H), 2.64 (m, 3H), 2.47 (m, 2H), 2.31 (m, 3H), 2.11 (m, 1H), 1.77 (m, 2H), 1.56 (m, 3H), 1.31 (d, 6H, J=6.0 Hz), 1.15 (m, 1H), 0.94 (m, 1H), 0.73 (d, 3H, J=6.9 Hz).

(−)-3-[(1R,4S,5S, 7R)-7-amino-4-methyl-2-(3-phenylpropyl)-2-azabicyclo[3.3.1]non-5-yl]phenol (23)

A solution of 22 (1 eq) (2.53 g, 6.23 mmole) in glacial acetic acid (8 mL/g of 22) and 48% HBr (8 mL/g of 22) was heated to reflux for 15 h. The reaction mixture was allowed to cool to room temperature added to ice (40 g/g of 22) and adjusted to pH=10 with 50% NaOH. The aqueous layer was extracted with 3:1 n-butanol/toluene (3×40 mL/g of 22), the organic layer was collected, dried (Na₂SO₄) and the solvent removed under reduced pressure. The product was purified by flash chromatography (50% (80% CHCl₃:18% CH₃OH:2% NH₄OH) in CH₂Cl₂) to afford 23 (84%) as yellow oil. $[\alpha]^{20}_D$−40.8° (cl.04, CHCl₃). ¹H-NMR (CDCl₃) δ7.27-7.07 (m, 6H), 6.65-6.58 (m, 3H), 4.33 (br., 2H), 3.54 (br., 1H), 2.79 (m, 1H), 2.66-2.53 (m, 3H), 2.46 (t, 2H, J=7.0 Hz), 2.31 (m, 3H), 2.04 (br., 1H), 1.77 (t, 2H, J=7.2), 1.53 (m, 1H), 1.14 (m, 1H), 0.98 (m, 1H), 0.70 (d, 3H, J=6.9 Hz); ¹³C-NMR (CDCl₃) δ157.5, 151.8, 142.8, 129.7, 128.7, 126.1, 116.7, 113.9, 113.1, 56.3, 54.7, 53.9, 52.1, 47.2, 40.8, 38.1, 33.8, 33.0, 29.4, 19.1.

(−)-N-[(1R,4S,5S,7R)-5-(3-hydroxy)phenyl-4-methyl-2-(3-phenylpropyl)-2-azabicyclo[3.3.1]non-7-yl]-3-(1-piperidinyl)propanamide (12)

BOP reagent (1.1 eq) was added to a solution of 23 (1 eq), 1-piperidinepropionic acid (2 eq) and triethylamine (5 eq) in dry THF (250 mL/g of 23). The reaction mixture was stirred under N₂ at room temperature for 4 h. The mixture was diluted with Et₂O (20 mL), washed with saturated NaHCO₃, followed by water. The organic layers were collected, dried (Na₂SO₄) and the solvent was removed under reduced pressure. The product was purified by flash chromatography (33% (80% CHCl₃:18% CH₃OH:2% NH₄OH) in CHCl₃) to afford 12 (85%) as an off-white foam.
¹H-NMR (CDCl₃) δ8.70 (br., 1H), 7.27-7.13 (m, 6H), 6.90-6.67 (m, 3H), 4.64 (m, 1H), 3.22 (br., 1H), 3.05 (m, 1H), 2.80-2.02 (m, 14H), 1.82-1.34 (m, 10H), 1.31-0.97 (m, 4H), 0.72 (d, 3H, J=6.9 Hz); LRMS (ES) m/z 504.5 (M+H)⁺.

4-(dimethylamino)-N-[(1R,4S,5S,7R)-5-(3-hydroxyphenyl)-4-methyl-2-(3-phenylpropyl)-2-azabicyclo[3.3.1]non-7-yl]butanamide (13)

BOP reagent (27 mg, 0.060 mmol) was added to a solution of (+)-7-amino-4-methyl-5-(3-hydroxyphenyl)-2-(3-phenylpropyl)-2-azabicyclo[3.3.1]nonane (23, 20 mg, 0.055 mmol), 4-(dimethylamino)butyric acid hydrochloride (18 mg, 0.11 mmol) and triethylamine (0.038 mL, 0.27 mmol) in dry THF (5 mL). The reaction mixture was stirred under N₂ at room temperature for 4 h. The mixture was diluted with Et₂O (20 mL), washed with saturated NaHCO₃, followed by water, organic layer collected, dried (Na₂SO₄) and solvent removed under reduced pressure yielding crude product. This was purified by flash chromatography (33% (80% CHCl₃:18% CH₃OH:2% NH₄OH) in CHCl₃) to afford 4-(dimethylamino)-N-[(1R,4S,5S,7R)-5-(3-hydroxyphenyl)-4-methyl-2-(3-phenylpropyl)-2-azabicyclo[3.3.1]non-7-yl]butanamide (13) (23 mg, 89%) as an off-white foam. ¹H-NMR (CDCl₃) δ7.28-7.09 (m, 6H), 6.89 (d, 1H, J=7.0 Hz), 6.64-6.59 (m, 3H), 6.31 (m, 1H), 4.65 (br., 1H), 3.16 (br., 1H), 3.02 (d, 1H, J=7.8 Hz), 2.69-2.14 (m, 16H), 1.91 (m, 1H), 1.86-1.75 (m, 4H), 1.58 (m 1H), 1.36-0.83 (m, 3H), 0.71 (d, 3H, J=6.5 Hz); LRMS (ES) m/z 478.7 (M+H)⁺.

REFERENCES (1) Aldrich, J. V. Analgesics. In *Burger's Medicinal Chemistry and Drug Discovery,* Wolff, M. E. Eds.; John Wiley & Sons: New York, 1996; Vol. 3.
(2) Pert, C. B.; Snyder, S. H. Opiate receptor: Demonstration in nervous tissue. *Science* 1973, 179, 1011–1014.
(3) Chen, Y.; Mestek, A.; Liu, J.; Hurley, J. A.; Yu, L. Molecular cloning and functional expression of a μ-opioid receptor from rat brain. *Mol. Pharmacol.* 1993, 44, 8–12.
(4) Thompson, R. C.; Mansour, A.; Akil. H.; Watson, S. J. Cloning and pharmacological characterization of a rat mu opioid receptor. *Neuron* 1993, 11(5), 903–13.
(5) Wang, J. B.; Johnson, P. S.; Persico, A. M.; Hawkins, A. L.; Griffin, C. A.; Uhl, G. R. Human μ opiate receptor: cDNA and genomic clones, pharmacological characterization and chromosomal assignment. *FEBS Lett.* 1994, 338, 217–222.
(6) Keiffer, B. L.; Befort. K.; Gaveriaux-Ruff, C.; Hirth, C. G. The δ-opioid receptor: Isolation of a cDNA by expression cloning and pharmacological characterization. *Proc. Natl Acad. Sci. U.S.A.* 1992, 89,12048–12052.
(7) Evans, C. J.; Keith, D. E., Jr.; Morrison, H.; Magendzo, K.; Edwards, R. H. Cloning of a delta opioid receptor by functional expression. *Science* 1992, 258, 1952–1955.
(8) Meng, F.; Xie, G. X.; Thompson, R. C.; Mansour. A.; Goldstein, A.; Watson, S. J.; Akil, H. Cloning and pharmacological characterization of a rat kappa opioid receptor. *Proc Natl Acad Sci USA* 1993, 90(21), 9954–8.
(9) Minami, M.; Toya, T.; Katao, Y.; Maekawa, K.; Nakamura, S.; Onogi, T.; Kaneko, S.; Satoh, M. Cloning and expression of a cDNA for the rat kappa-opioid receptor. *FEBS Lett* 1993, 329(3), 291–5.
(10) Nishi, M.; Takeshima, H.; Fukuda, K.; Kato, S.; Mori K. cDNA cloning and pharmacological characterization of an opioid receptor with high affinities for kappa-subtype-selective ligands. *FEBS Lett* 1993, 330(1), 77–80.
(11) Nunez, G.; Urzua, J. [Opioids and the immune system]. *Rev Med Chil* 1999, 127(3), 341–8.
(12) Bruce, D. S.; Bailey, E. C.; Setran, D. P.; Tramell, M. S.; Jacobson, D.; Oeltgen, P. R.; Horton, N. D.; Hellgren, E. C. Circannual variations in bear plasma albumin and its opioid-like effects on guinea pig ileum. *Pharmacol Biochem Behav* 1996, 53(4), 885–9.
(13) Volpicelli, J. R.; Alterman, A. I.; Hayashida M.; O'Brien, C. P. Naltrexone in the treatment of alcohol dependence. *Arch. Gen. Psychiatry* 1992, 49, 876–879.
(14) Volpicelli, J. R.; Watson, N. T.; King, A. C.; Sherman, C. E.; O'Brien, C. P. Effect of naltrexone on alcohol "high" in alcoholics. *Am. J. Psychiatry* 1995,152, 613–615.
(15) Marki, A.; Monory, K.; Otvos, F.; Toth, G.; Krassnig, R.; Schmidhammer, H.; Traynor, J.R.; Roques, B.P.; Maldonado, R.; Borsodi, A. Mu-opioid receptor specific antagonist cyprodime: characterization by in vitro radioligand and [35S]GTPgammaS binding assays. *Eur J Pharmacol* 1999, 383(2), 209–14.

(16) Portoghese, P. S. The design of δ-selective opioid receptor antagonists. *Il Farmaco* 1993, 48(2), 243–251.

(17) Portoghese, P. S.; Lipkowski, A. W.; Takemori, A. E. Binaltorphimine and nor-binaltorphimine, potent and selective κ-opioid receptor antagonists. *Life Sci.* 1987, 40(13), 1287–1292.

(18) Olmsted, S. L.; Takemori, A. E.; Portoghese, P. S. A remarkable change of opioid receptor selectivity on the attachment of a peptidomimetic κ address element to the δ antagonist, natrindole: 5'-[N²-alkylamidino)methyl] naltrindole derivatives as a novel class of κ opioid receptor antagonists. *J. Med. Chem.* 1993, 36(1),179–180.

(19) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J Med Chem* 1998, 41(25), 4911–4.

(20) Schwyzer, R. ACTH: A short introductory review. *Ann. N.Y. Acad. Sci.* 1977, 247, 3–26.

(21) Trujillo, K. A.; Akil, H. Changes in prodynorphin peptide content following treatment with morphine or amphetamine: possible role in mechanisms of action of drug of abuse. *NIDA Res Monogr* 1989, 95, 550–1.

(22) Smiley, P. L.; Johnson, M.; Bush, L.; Gibb, J. W.; Hanson, G. R. Effects of cocaine on extrapyramidal and limbic dynorphin systems. *J Pharmacol Exp Ther* 1990, 253(3), 938–43.

(23) Corbett, A. D.; Paterson, S. J.; McKnight, A. T.; Magnan, J.; Kosterlitz, H. W. Dynorphin and dynorphin are ligands for the kappa-subtype of opiate receptor. *Nature* 1982, 299(5878), 79–81.

(24) Spanagel, R.; Herz, A.; Shippinberg, T. A. Opposing tonically active endogenous opioid systems modulate the mesolimbic dopaminergic pathway. *Proc. Natl. Acad. Sci. U.S.A.* 1992, 89, 2046–2050.

(25) Spanagel, R.; Shippenberg, T. S. Modulation of morphine-induced sensitization by endogenous κ opioid systems in the rat. *Neurosci. Lett.* 1993, 153, 232–236.

(26) Zadina, J. E.; Hackler, L.; Ge, L.-J.; Kastin, A. J. A potent and selective endogenous agonist for the μ-opiate receptor. *Nature* 1997, 386, 499–502.

(27) Zimmerman, D. M.; Nickander, R.; Horng, J. S.; Wong, D. T. New structural concepts for narcotic antagonists defined in a 4-phenylpiperidine series. *Nature* 1978, 275. 332–334.

(28) Zimmerman, D. M.; Smits, S.; Nickander, R. Further investigation of novel 3-methyl-4-phenylpiperidine narcotic antagonists. In *Proceedings of the 40th Annual Scientific Meeting of the Committee on Problems of Drug Dependence,* 1978, pp. 237–247.

(29) Zimmerman, D. M.; Smits, S. E.; Hynes. M. D.; Cantrell, B. E.; Reamer, M.; Nickander Structural requirements for affinity and intrinsic activity at the opiate receptor defined in 4-phenylpiperidine and related series. In *Problems of Drug Dependence* 1981, *Proceedings of the 43rd Annual Scientific Meeting of the Committee on Problems of Drug Dependence, Inc.,* Harris, L. S. Eds.; 1981, pp. 112–116.

(30) Zimmerman, D. M.; Smits, S. E.; Hynes, M. D.; Cantrell, B. E.; Reamer, M.; Nickander, R. Structural requirements for affinity and intrinsic activity at the opiate receptor defined in 4-phenylpiperidine and related series. In *Problems of Drug Dependence,* 1981, *Proceedings of the 43rd Annual Scientific Meeting, The committee on Problems of Drug Dependence, Inc., Harris, L. S. Eds., Committee on Problems of Drug Dependence, Inc.:* 1982; Vol. NIDA Research Monograph 41, pp. 112–118.

(31) Zimmerman, D. M.; Cantrell, B. E.; Swartzendruber, J. K.; Jones, N. D.; Mendelsohn, L. G.; Leander, J. D.; Nickander, R. C. Synthesis and analgesic properties of N-substituted trans-4a-aryldecahydroisoquinolines. *J. Med. Chem.* 1988, 31, 555–560.

(32) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993, 36(20), 2833–2841.

(33) Zimmerman, D. M.; Hermann, R. B.; Mitch, C. H.; Shaw, W. N.; Mendelsohn, L. G.; Leander, J. D. Opioid receptor antagonists: Comparison of trans-3,4-dimethyl-4-phenylpiperidines and their use in the development of a model of opioid receptors. *Pharmacol. Rev.* in press.

(34) Thomas, J. B.; Zheng, X.; MascareHa, S. W.; Rothman, R. B.; Dersch, C. M.; Partilla, J. S.; Flippen-Anderson, J. L.; George, C. F.; Cantrell, B. E.; Zimmerman, D. M.; Carroll, F. I. N-Substituted 9β-methyl-5-(3-hydroxyphenyl)morphans are opioid receptor pure antagonists. *J. Med. Chem.* 1998, 41(21), 4143–4149.

(35) Werner, J. A.; Cerbone, L. R.; Frank, S. A.; Ward, J. A.; Labib, P.; Tharp-Taylor, R. W.; Ryan, C. W. Synthesis of trans-3,4-dimethyl-4-(3-hydroxyphenyl)piperidine opioid antagonists: Application of the cis-thermal elimination of carbonates to alkaloid synthesis. *J. Org. Chem.* 1996, 61, 587–597.

(36) Gu, X.-P.;Ikeda, I.;Komada, S.; Masuyama, A.; Okahara, M. *J. Org. Chem.* 1986, 51, 5425.

(37) Gu, X.-P.; Nishida, N., Ikeda, I., Okahara, M. 2-(Chloromethyl)-3,5-dioxahex-1-ene. An effective acetonylating reagent. *J. Org. Chem.* 1987, 52,3192–3196.

(38) Gu, X.-P.; Okuhara, T.; Ikeda, I.; Okahara, M. Catalytic acetonylation of cyclic 1.3-dicarbonyl-systems by 2-(chloromethyl)-3,5-dioxa-1-hexene. *Synthesis* 1988, 535–537.

(39) Thomas, J. B.; Gigstad, K. M.; Fix, S. E.; Burgess, J. P.; Cooper, J. B.; Mascarella, S. W.; Cantrell, B. E.; Zimmerman, D. M.; Carroll, F. I. A stereoselective synthetic approach to N-alkyl-4β-methyl-5-phenylmorphans. *Tetrahedron Lett.* 1999, 40(3), 403–406.

(40) Abdel-Magid, A. F.; Carson, K., G.; Harris, B. D.; Maryanoff, C. A.; Shah, R. D. Reductive animation of aldehydes and ketones with sodium triacetoxyborohydride. Studies on direct and indirect reductive animation procedures. *J. Org. Chem.* 1996, 61, 3849–3862.

(41) Bertha, C. M.; Ellis, M.; Flippen-Anderson, J. L.; Porreca, F.; Rothman, R. B.; Davis, P.; Xu, H.; Becketts, K.; Rice, K. C. Probes for narcotic receptor-mediated phenomena. 21. Novel derivatives of 3-(1,2,3,4,5,11-hexahydro-3-methyl-2,6-methano-6H-azocino[4,5-b]indol-6-yl)phenols with improved δ opioid receptor selectivity. *J. Med. Chem.* 1996, 39, 2081–2086.

(42) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R, 4R)-dimethyl4-(3-hydroxyphenyl)piperidine opioid antagonists. *J. Med. Chem.* 1998, 41(11), 1980–1990.

Obviously, numerous modifications and variations of the present invention are possible in light of the above teachings. It is therefore to be understood that within the scope of the appended claims, the invention may be practiced otherwise than as specifically described herein.

What is claimed is:

1. A method of inducing kappa opioid receptor antagonism in a subject in need thereof, comprising:

administering to said subject a composition comprising a kappa opioid receptor antagonist and a physiologically acceptable carrier, wherein the kappa opioid receptor antagonist is a compound of formula (I):

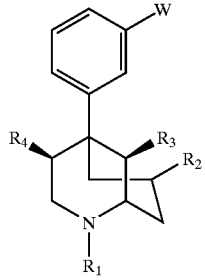

wherein $R_1$ is $C_{2-8}$ alkyl, $C_{3-8}$ alkenyl, $C_{3-8}$ alkynyl, $C_{1-8}$ alkylaryl or one of the following groups:

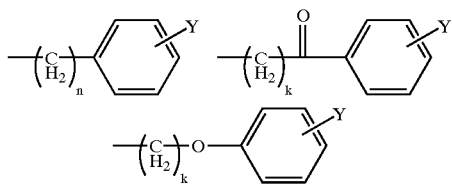

$R_2$ is a member selected from the group consisting of formulae (a)–(pp):

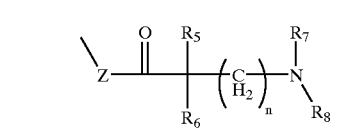
(a)

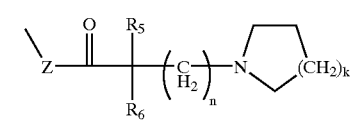
(b)

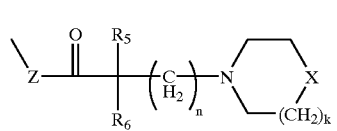
(c)

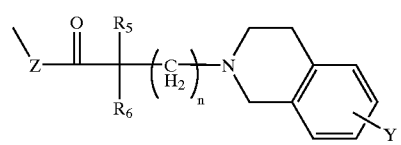
(d)

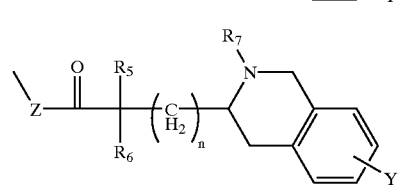
(e)

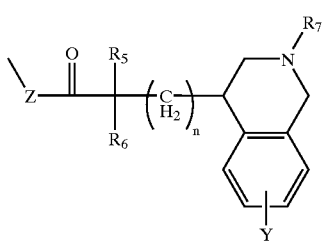
(f)

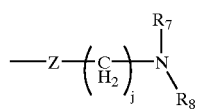
(g)

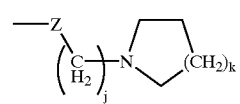
(h)

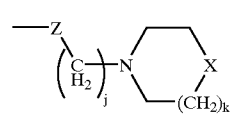
(i)

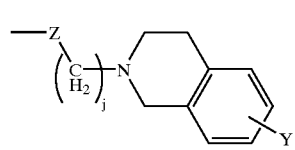
(j)

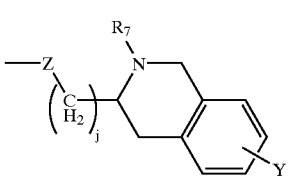
(k)

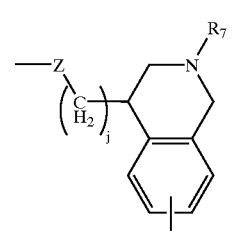
(l)

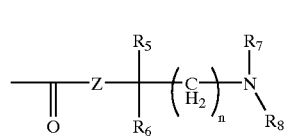
(m)

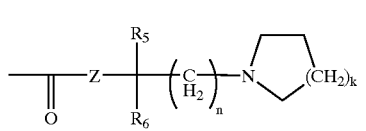
(n)

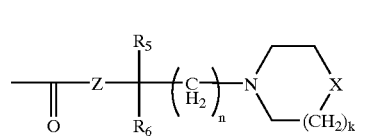
(o)

-continued

-continued

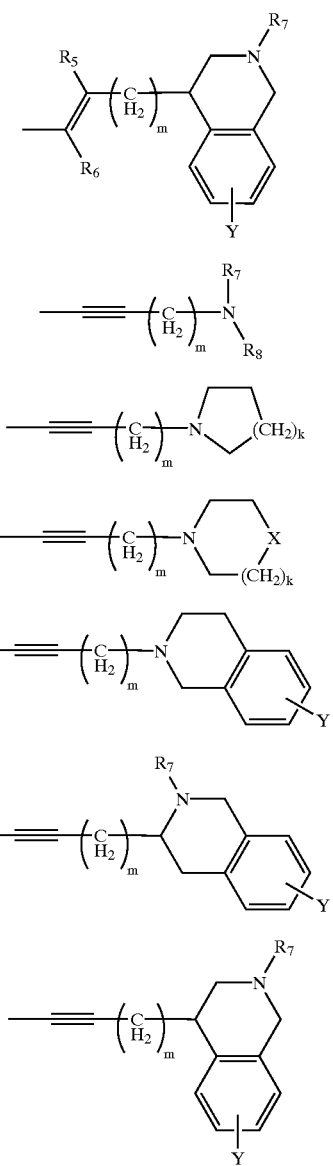

X is NR, O or S;
Y is OH, OR$_9$, C$_{1-8}$ alkyl, F, Cl, or CF$_3$;
R is hydrogen, C$_{1-8}$ alkyl, C$_{3-8}$ alkenyl, C3-8 alkynyl, C$_{1-8}$ alkylaryl, CO$_2$R$_9$
W is a member selected from the group consisting of: H, OH, OCOR$_9$; amino, —NR$_3$SO$_2$R$_9$ and —NR$_3$CO$_2$R$_9$;
Z is NR$_3$ or O;
n is 1, 2 or 3;
m is 1, 2, 3 or 4;
j is 2, 3 or 4;
k is 1 or 2;
R$_3$ is hydrogen, C$_{1-8}$ alkyl, C$_{3-8}$ alkenyl, C$_{3-8}$ alkynyl, or C$_{1-8}$ alkylaryl;
R$_4$ is hydrogen, C$_{1-8}$ alkyl, C$_{3-8}$ alkenyl, C$_{3-8}$ alkynyl, or C1-8 alkylaryl;
R$_5$ and R$_6$ are each independently, hydrogen, C$_{1-8}$ alkyl, C$_{3-8}$ alkenyl, C$_{3-8}$ alkynyl, or C$_{1-8}$ alkylaryl;
R$_7$ and R$_8$ are each independently, hydrogen, C$_{1-8}$ alkyl, C$_{3-8}$ alkenyl, C$_{3-8}$ alkynyl, or C$_{1-8}$ alkylaryl; and R$_9$ is C$_{1-8}$ alkyl, C$_{3-8}$ alkenyl, C$_{3-8}$ alkynyl, or C$_{1-8}$ alkylaryl.

2. The method of claim 1, wherein said kappa opioid receptor antagonist is a compound of formula I, wherein:
R$_1$, X, Y, R, W, Z, n, m, j, k, and R$_5$–R$_9$ are as stated;
R$_2$ is a member selected from the group consisting of formulae (a)–(jj)
R$_3$ is hydrogen, or C$_{1-8}$ alkyl; and
R$_4$ is hydrogen, or C$_{1-8}$ alkyl.

3. The method of claim 1, wherein said kappa opioid receptor antagonist is a compound of formula I:
wherein X, Y, W, Z, n, m, j, k, and R$_9$ are as stated;
R$_1$ is C$_{2-8}$ alkyl, C$_{3-8}$ alkenyl, or a group of the following formulae:

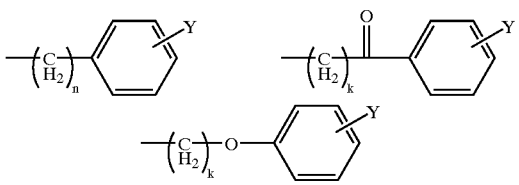

R$_2$ is a member selected from the group consisting of formulae (a)–(dd);
R is hydrogen, C$_{1-8}$ alkyl, C$_{1-8}$ alkylaryl, or CO$_2$R$_9$;
R$_3$ is hydrogen, or C$_{1-8}$ alkyl;
R$_4$ is hydrogen, or C$_{1-8}$ alkyl;
R$_5$ and R$_6$ are each independently, hydrogen, C$_{1-8}$ alkyl, or C$_{1-8}$ alkylaryl; and
R$_7$ and R$_8$ are each independently, hydrogen, C$_{1-8}$ alkyl, or C$_{1-8}$ alkylaryl.

4. The method of claim 1, wherein said kappa opioid receptor antagonist is a compound of formula I:
wherein X, Y, Z, n, m, j, k, and R$_9$ are as stated;
R$_1$ is C$_{2-8}$ alkyl, C$_{3-8}$ alkenyl, or a group selected from the following formulae:

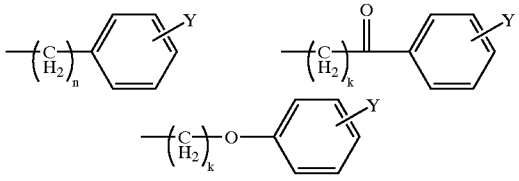

R$_2$ is a member selected from the group consisting of formulae (a)–(r);
R is hydrogen, C$_{1-8}$ alkyl, C$_{1-8}$ alkylaryl, or CO$_2$R$_9$;
W is OH or OCOR$_9$;
R$_3$ is hydrogen, or C$_{1-4}$ alkyl;
R$_4$ is hydrogen or C$_{1-4}$ alkyl;
R$_5$ and R$_6$ are each independently, hydrogen, or C$_{1-4}$ alkyl; and
R$_7$ and R$_8$ are each independently, hydrogen, or C$_{1-4}$ alkyl.

5. The method of claim 1, wherein said kappa opioid receptor antagonist is a compound of formula I:
wherein X, Y, Z, n, m, j, k, and R$_9$ are as stated;
R$_1$ is C$_{2-8}$ alkyl, C$_{3-8}$ alkenyl, C$_{1-4}$ alkylaryl or a member selected from the following formulae:

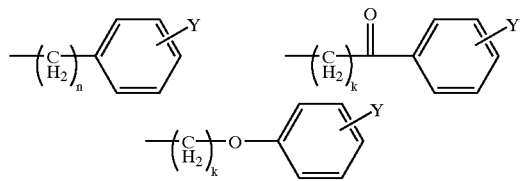

$R_2$ is a member selected from the group consisting of formulae (a)–(i);

R is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$ and $R_6$ are each independently, hydrogen, or $C_{1-4}$ alkyl; and $R_7$ and $R_8$ are each independently, hydrogen, or $C_{1-4}$ alkyl.

6. The method of claim 1, wherein said kappa opioid receptor antagonist is a compound of formula I:

wherein X, Y, Z, n, m, j, k, and $R_9$ are as stated;

$R_1$ is $C_{2-8}$ alkyl, $C_{3-8}$ alkenyl, $C_{1-4}$ alkylaryl, or a member selected from the following formulae:

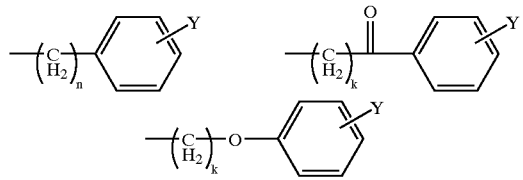

$R_2$ is a member selected from the group consisting of formulae (a)–(f);

R is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$, $R_6$, $R_7$ and $R_8$ are each, independently, H or $C_{1-4}$ alkyl.

7. A kappa opioid receptor antagonist compound represented by the formula (I):

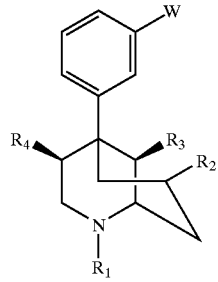

wherein $R_1$ is $C_{2-8}$ alkyl, $C_{3-8}$ alkenyl, $C_{1-8}$ alkynyl, $C_{1-8}$ alkylaryl or one of the following groups:

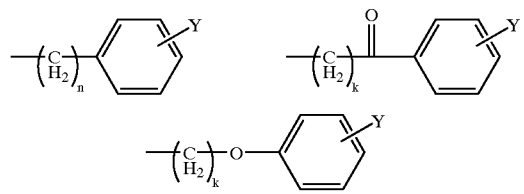

$R_2$ is a member selected from the group consisting of formulae (a)–(pp):

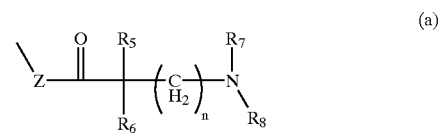
(a)

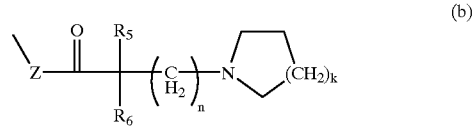
(b)

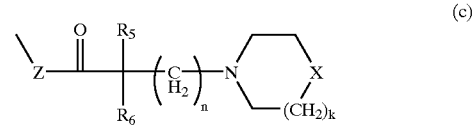
(c)

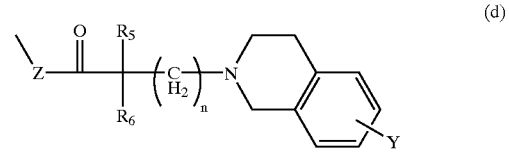
(d)

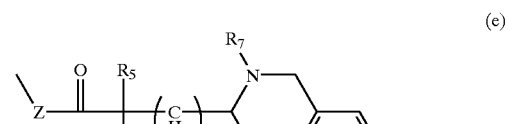
(e)

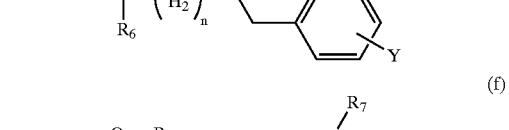
(f)

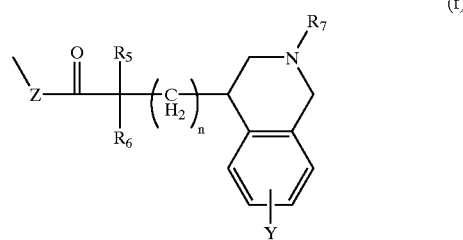
(g)

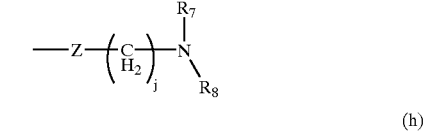
(h)

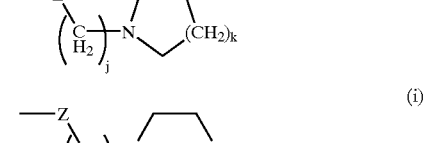
(i)

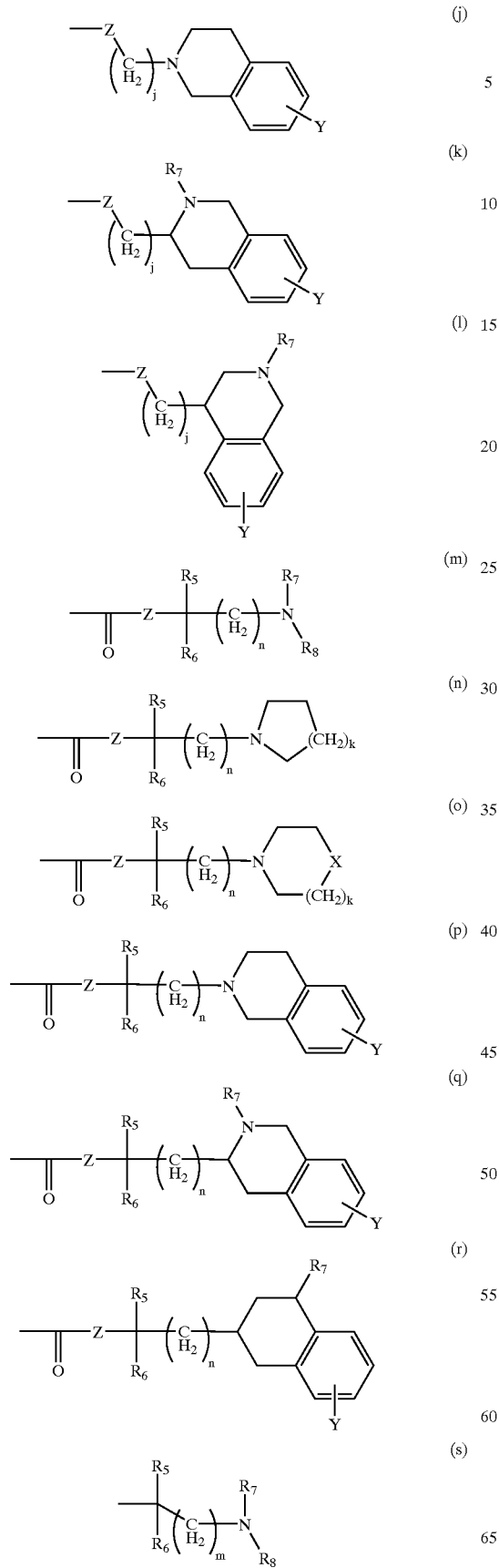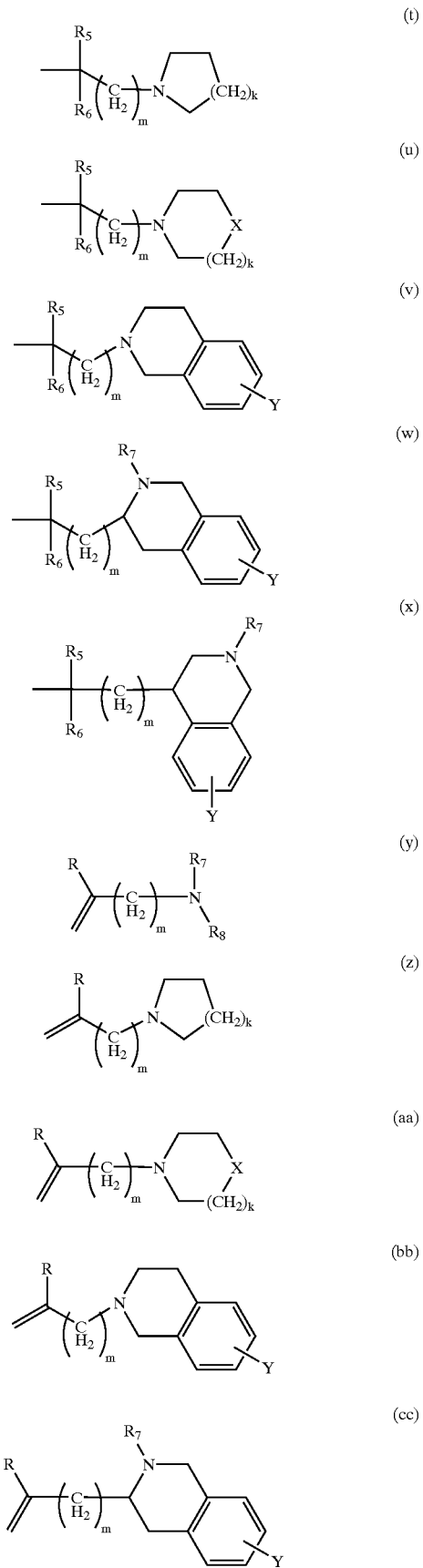

X is NR, O or S;

Y is OH, OR$_9$, C$_{1-8}$ alkyl, F, Cl, or CF$_3$;

R is hydrogen, C$_{1-8}$ alkyl, C$_{3-8}$ alkenyl, C$_{3-8}$ alkynyl, C$_{1-8}$ alkylaryl, CO$_2$R$_9$ W is a member selected from the group consisting of: H, OH, COOR$_9$; amino, —NR$_3$SO$_2$R$_9$ and —NR$_3$CO$_2$R$_9$;

Z is NR$_3$ or O;

n is 1, 2 or 3;

m is 1, 2, 3 or 4;

j is 2, 3 or 4;

k is 1 or 2;

R$_3$ is hydrogen, C$_{1-8}$ alkyl, C$_{3-8}$ alkenyl, C$_{3-8}$ alkynyl, or C$_{1-8}$ alkylaryl;

R$_4$ is hydrogen, C$_{1-8}$ alkyl, C$_{3-8}$ alkenyl, C$_{3-8}$ alkynyl, or C$_{1-8}$ alkylaryl;

R$_5$ and R$_6$ are each independently, hydrogen, C$_{1-8}$ alkyl, C$_{3-8}$ alkenyl, C$_{3-8}$ alkynyl, or C$_{1-8}$ alkylaryl;

R$_7$ and R$_8$ are each independently, hydrogen, C$_{1-8}$ alkyl, C$_{3-8}$ alkenyl, C$_{3-8}$ alkynyl, or C$_{1-8}$ alkylaryl; and R$_9$ is C$_{1-8}$ alkyl, C$_{3-8}$ alkenyl, C$_{3-8}$ alkynyl, or C$_{1-8}$ alkylaryl.

8. The kappa opioid receptor antagonist of claim 7, wherein said compound is a compound of formula I:

wherein R$_1$, X, Y, R, W, Z, n, m, j, k, and R$_5$–R$_9$ are the as stated;

R$_2$ is a member selected from the group consisting of formulae (a)–(jj)

R$_3$ is hydrogen, or C$_{1-8}$ alkyl; and

R$_4$ is hydrogen, or C$_{1-8}$ alkyl.

9. The kappa opioid receptor antagonist of claim 7, wherein said compound is a compound of formula I:

wherein X, Y, W, Z, n, m, j, k, and R$_9$ are as stated:

R$_1$ is C$_{2-8}$ alkyl, C$_{3-8}$ alkenyl, or a group of the following formulae:

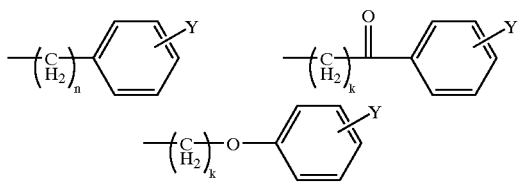

$R_2$ is a member selected from the group consisting of formulae (a)–(dd);

$R$ is hydrogen, $C_{1-8}$ alkyl, $C_{1-8}$ alkylaryl, or $CO_2R_9$;

$R_3$ is hydrogen, or $C_{1-8}$ alkyl;

$R_4$ is hydrogen, or $C_{1-8}$ alkyl;

$R_5$ and $R_6$ are each independently, hydrogen, $C_{1-8}$ alkyl, or $C_{1-8}$ alkylaryl; and $R_7$ and $R_8$ are each independently, hydrogen, $C_{1-8}$ alkyl, or $C_{1-8}$ alkylaryl.

10. The kappa opioid receptor antagonist of claim 7, wherein said compound is a compound of formula I:

wherein X, Y, Z, n, m, j, k, and $R_9$ are as stated;

$R_1$ is $C_{2-8}$ alkyl, $C_{1-8}$ alkenyl, or a group selected from the following formulae:

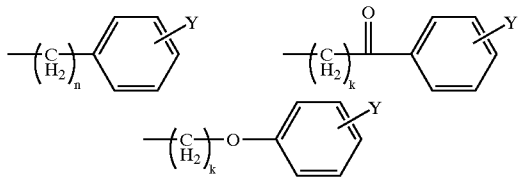

$R_2$ is a member selected from the group consisting of formulae (a)–(r);

$R$ is hydrogen, $C_{1-8}$ alkyl, $C_{1-8}$ alkylaryl, or $CO_2R_9$;

W is OH or $OCOR_9$;

$R_3$ is hydrogen, or $C_{1-4}$ alkyl;

$R_4$ is hydrogen or $C_{1-4}$ alkyl;

$R_5$ and $R_6$ are each independently, hydrogen, or $C_{1-4}$ alkyl; and $R_7$ and $R_8$ are each independently, hydrogen, or $C_{1-4}$ alkyl.

11. The kappa opioid receptor antagonist of claim 7, wherein said compound is a compound of formula I:

wherein X, Y, Z, n, m, j, k, and $R_9$ are as stated;

$R_1$ is $C_{2-8}$ alkyl, $C_{3-8}$ alkenyl, $C_{1-4}$ alkylaryl or a member selected from the following formulae:

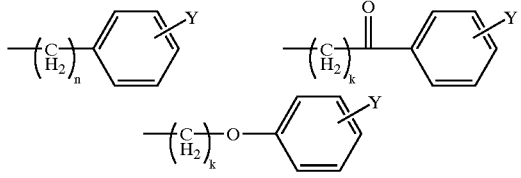

$R_2$ is a member selected from the group consisting of formulae (a)–(i);

$R$ is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$ and $R_6$ are each independently, hydrogen, or $C_{1-4}$ alkyl; and $R_7$ and $R_8$ are each independently, hydrogen, or $C_{1-4}$ alkyl.

12. The kappa opioid receptor antagonist of claim 7, wherein said compound is a compound of formula I:

wherein X, Y, Z, n, m, j, k, and $R_9$ are as stated, $R_1$ is $C_{2-8}$ alkyl, $C_{3-8}$ alkenyl, $C_{1-4}$ alkylaryl, or a member selected from the following formulae:

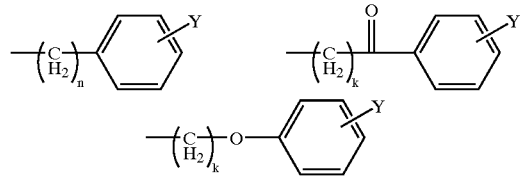

$R_2$ is a member selected from the group consisting of formulae (a)–(f);

$R$ is hydrogen, $C_{1-4}$ alkyl, $C_{1-4}$ alkylaryl, or $CO_2R_9$;

W is OH or $OCOR_9$;

$R_3$ is hydrogen, or methyl;

$R_4$ is hydrogen or methyl;

$R_5$, $R_6$, $R_7$ and $R_8$ are each, independently, H or $C_{1-4}$ alkyl.

13. A pharmaceutical composition comprising:

an effective amount of a kappa opioid receptor antagonist and a physiologically acceptable carrier, wherein the kappa opioid receptor antagonist is a compound of formula (I):

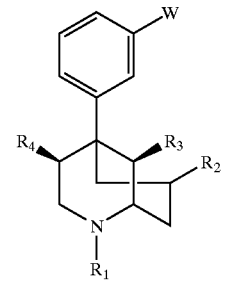

wherein $R_1$ is $C_{2-8}$ alkyl, $C_{3-8}$ alkenyl, $C_{3-8}$ alkynyl, $C_{1-8}$ alkylaryl or one of the following groups:

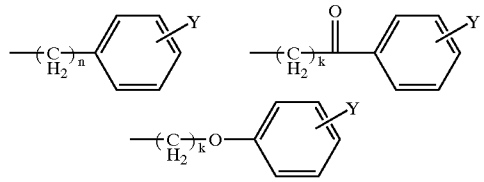

$R_2$ is a member selected from the group consisting of formulae (a)–(pp):

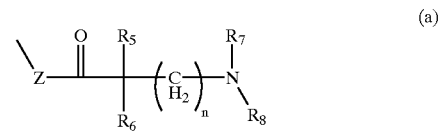

(a)

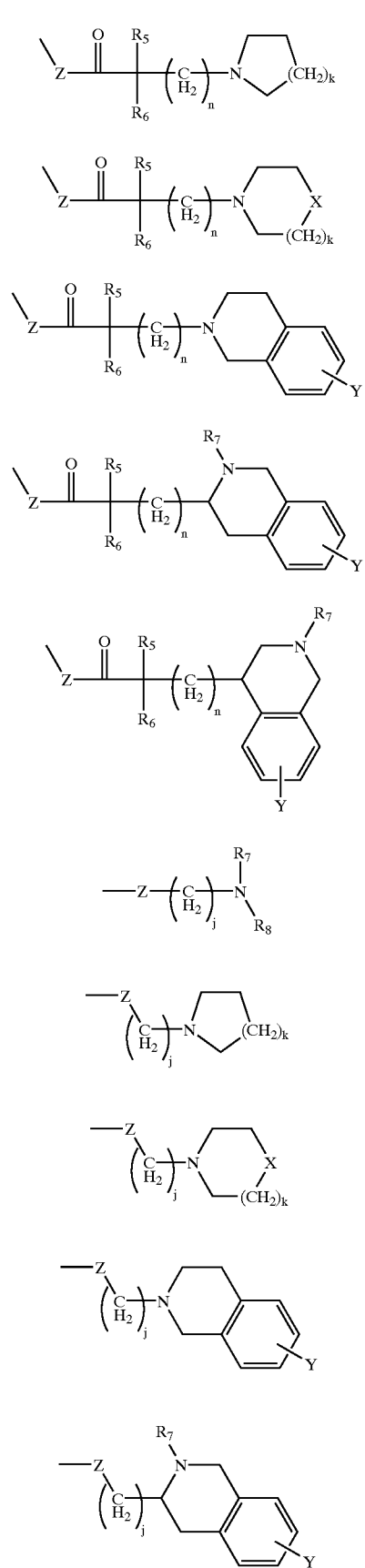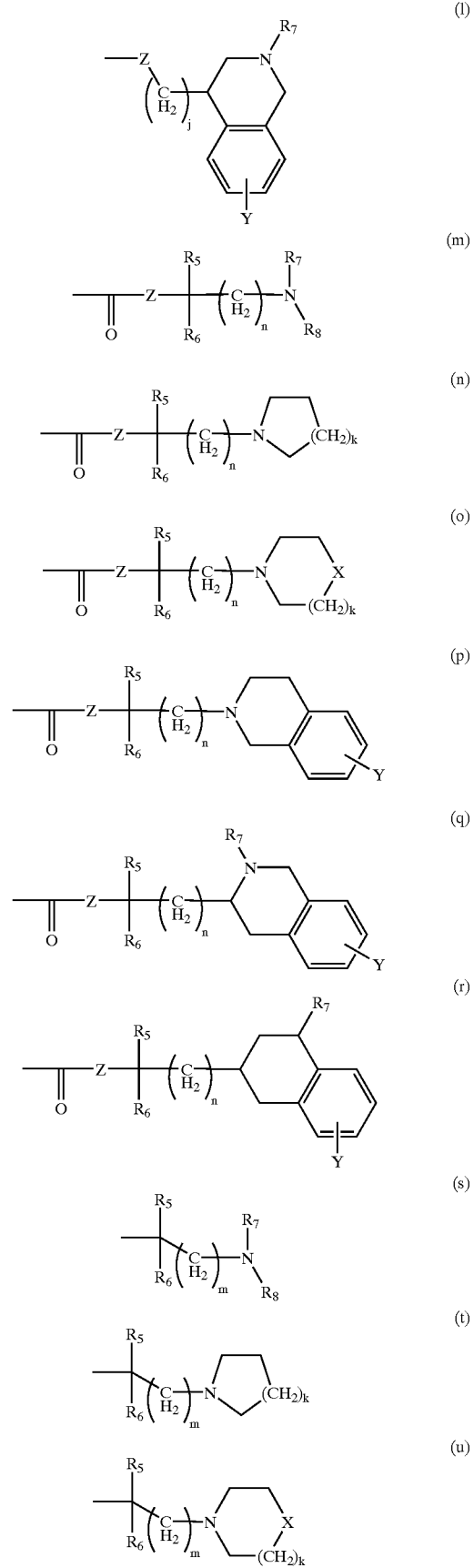

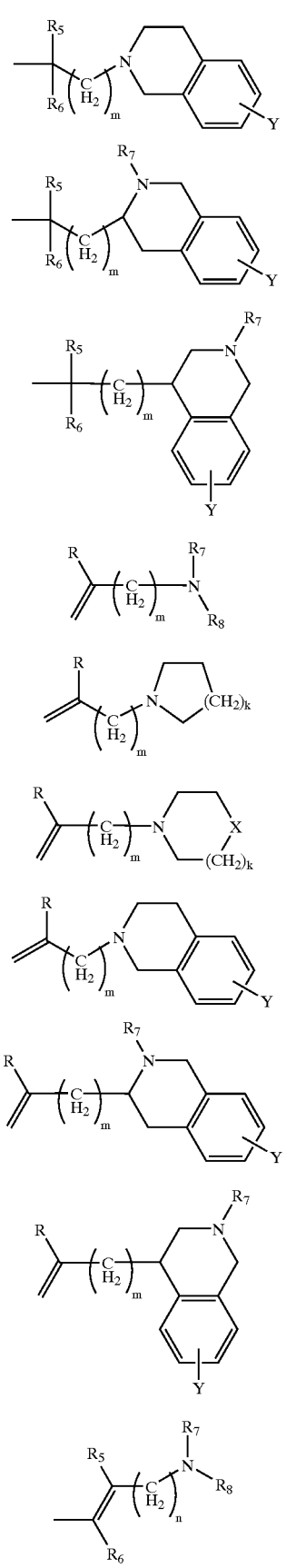
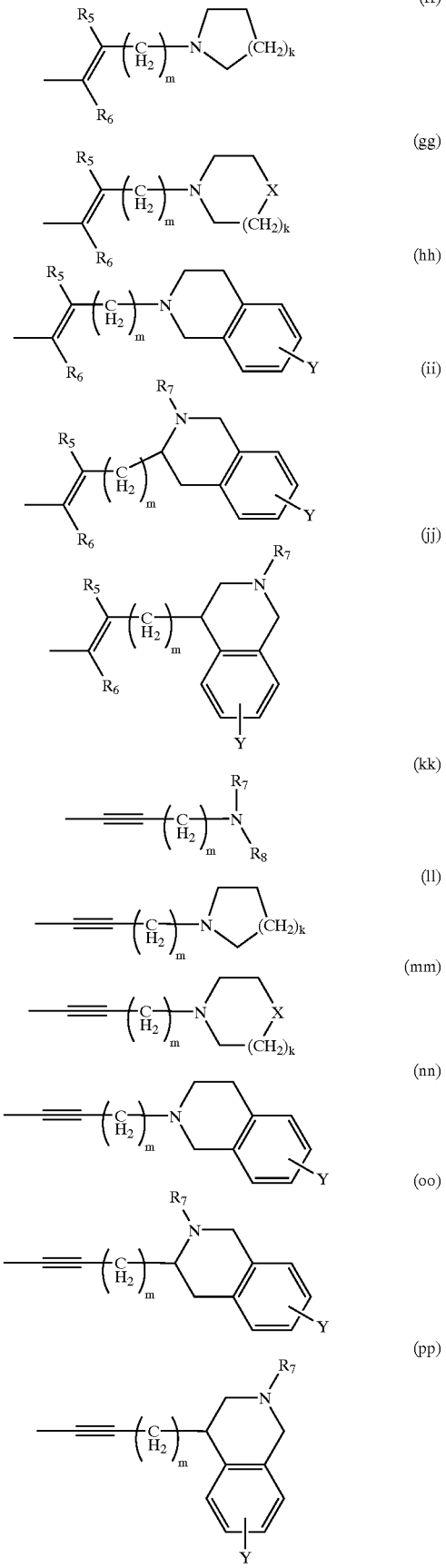

X is NR, O or S;
Y is OH, OR$_9$, C$_{1-8}$ alkyl, F, Cl, or CF$_3$;
R is hydrogen, C$_{1-8}$ alkyl, C$_{3-8}$ alkenyl, C$_{3-8}$ alkynyl, C$_{1-8}$ alkylaryl, CO$_2$R$_9$
W is a member selected from the group consisting of: H, OH, COOR$_9$; amino, —NR$_3$SO$_2$R$_9$ and —NR$_3$CO$_2$R$_9$;
Z is NR$_3$ or O;
n is 1, 2 or 3;
m is 1, 2, 3 or 4;
j is 2, 3 or 4;
k is 1 or 2;
R$_3$ is hydrogen, C$_{1-8}$ alkyl, C$_{3-8}$ alkenyl, C$_{3-8}$ alkynyl, or C$_{1-8}$ alkylaryl;
R$_4$ is hydrogen, C$_{1-8}$ alkyl, C$_{3-8}$ alkenyl, C$_{3-8}$ alkynyl, or C$_{1-8}$ alkylaryl;
R$_5$ and R$_6$ are each independently, hydrogen, C$_{1-8}$ alkyl, C$_{3-8}$ alkenyl, C$_{3-8}$ alkynyl, or C$_{1-8}$ alkylaryl;
R$_7$ and R$_8$ are each independently, hydrogen, C$_{1-8}$ alkyl, C$_{3-8}$ alkenyl, C$_{3-8}$ alkynyl, or C$_{1-8}$ alkylaryl; and
R$_9$ is C$_{1-8}$ alkyl, C$_{3-8}$ alkenyl, C$_{3-8}$ alkynyl, or C$_{1-8}$ alkylaryl.

14. The pharmaceutical composition of claim 13, wherein said kappa opioid receptor antagonist is a compound of formula I:
wherein R$_1$, X, Y, R, W, Z, n, m, j, k, and R$_5$–R$_9$ are as stated;
R$_2$ is a member selected from the group consisting of formulae (a)–(jj)
R$_3$ is hydrogen, or C$_{1-8}$ alkyl; and
R$_4$ is hydrogen, or C$_{1-8}$ alkyl.

15. The pharmaceutical composition of claim 13, wherein said kappa opioid receptor antagonist is a compound of formula I:
wherein X, Y, W, Z, n, m, j, k, and R$_9$ are as stated;
R$_1$ is C$_{2-8}$ alkyl, C$_{3-8}$ alkenyl, or a group of the following formulae:

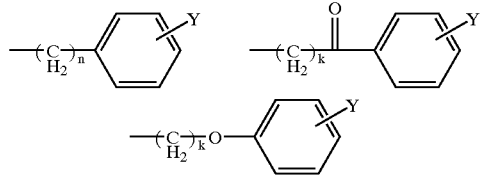

R$_2$ is a member selected from the group consisting of formulae (a)–(dd);
R is hydrogen, C$_{1-8}$ alkyl, C$_{1-8}$ alkylaryl, or CO$_2$R$_9$;
R$_3$ is hydrogen, or C$_{1-8}$ alkyl;
R$_4$ is hydrogen, or C$_{1-8}$ alkyl;
R$_5$ and R$_6$ are each independently, hydrogen, C$_{1-8}$ alkyl, or C$_{1-8}$ alkylaryl; and
R$_7$ and R$_8$ are each independently, hydrogen, C$_{1-8}$ alkyl, or C$_{1-8}$ alkylaryl.

16. The pharmaceutical composition of claim 13, wherein said kappa opioid receptor antagonist is a compound of formula I:
wherein X, Y, Z, n, m, j, k, and R$_9$ are as stated;
R$_1$ is C$_{2-8}$ alkyl, C$_{3-8}$ alkenyl, or a group selected from the following formulae:

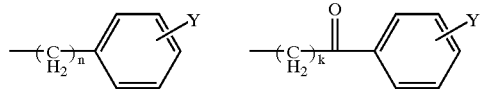

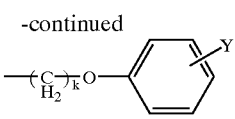

R$_2$ is a member selected from the group consisting of formulae (a)–(r);
R is hydrogen, C$_{1-8}$ alkyl, C$_{1-8}$ alkylaryl, or CO$_2$R$_9$;
W is OH or OCOR$_9$;
R$_3$ is hydrogen, or C$_{1-4}$ alkyl;
R$_4$ is hydrogen or C$_{1-4}$ alkyl;
R$_5$ and R$_6$ are each independently, hydrogen, or C$_{1-4}$ alkyl; and
R$_7$ and R$_8$ are each independently, hydrogen, or C$_{1-4}$ alkyl.

17. The pharmaceutical composition of claim 13, wherein said kappa opioid receptor antagonist is a compound of formula I:
wherein X, Y, Z, n, m, j, k, and R$_9$ are as stated;
R$_1$ is C$_{2-8}$ alkyl, C$_{3-8}$ alkenyl, C$_{1-4}$ alkylaryl or a member selected from the following formulae:

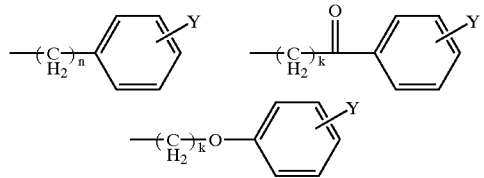

R$_2$ is a member selected from the group consisting of formulae (a)–(i);
R is hydrogen, C$_{1-4}$ alkyl, C$_{1-4}$ alkylaryl, or CO$_2$R$_9$;
W is OH or OCOR$_9$;
R$_3$ is hydrogen, or methyl;
R$_4$ is hydrogen or methyl;
R$_5$ and R$_6$ are each independently, hydrogen, or C$_{1-4}$ alkyl; and
R$_7$ and R$_8$ are each independently, hydrogen, or C$_{1-4}$ alkyl.

18. The pharmaceutical composition of claim 13, wherein said kappa opioid receptor antagonist is a compound of formula I:
wherein X, Y, Z, n, m, j, k, and R$_9$ are as stated;
R$_1$ is C$_{2-8}$ alkyl, C$_{3-8}$ alkenyl, C$_{1-4}$ alkylaryl, or a member selected from the following formulae:

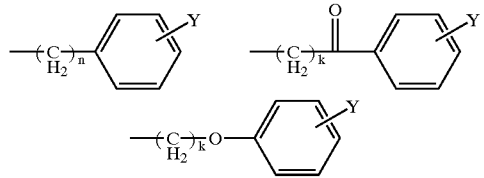

R$_2$ is a member selected from the group consisting of formulae (a)–(f);
R is hydrogen, C$_{1-4}$ alkyl, C$_{1-4}$ alkylaryl, or CO$_2$R$_9$;
W is OH or OCOR$_9$;
R$_3$ is hydrogen, or methyl;
R$_4$ is hydrogen or methyl;
R$_5$, R$_6$, R$_7$ and R$_8$ are each, independently, H or C$_{1-4}$ alkyl.

19. The pharmaceutical composition of claim 13, wherein said composition is an injectable composition.

20. The pharmaceutical composition of claim 13, wherein said composition is an orally administrable composition.

21. The pharmaceutical composition of claim 20, wherein said orally administrable composition is in a form selected from the group consisting of tablets, capsules, troches, powders, solutions, dispersions, emulsions and suspensions.

22. A method of inducing kappa opioid receptor antagonism in a subject in need thereof, comprising:

administering to said subject a composition comprising a kappa opioid receptor antagonist and a physiologically acceptable carrier, wherein the kappa opioid receptor antagonist is a compound of formula 12 or 13

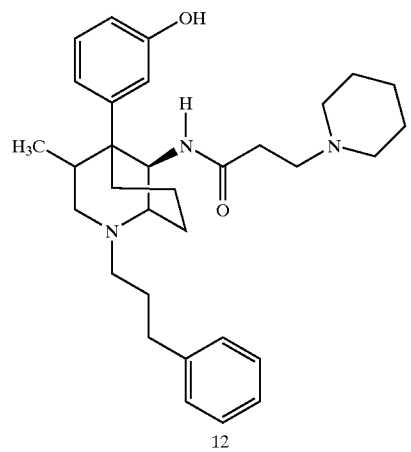
12

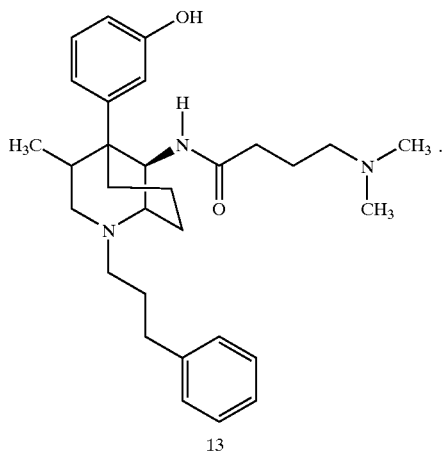
13

23. A kappa opioid receptor antagonist compound represented by formula 12 or 13

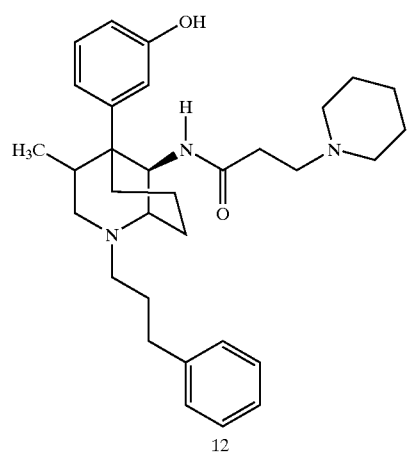
12

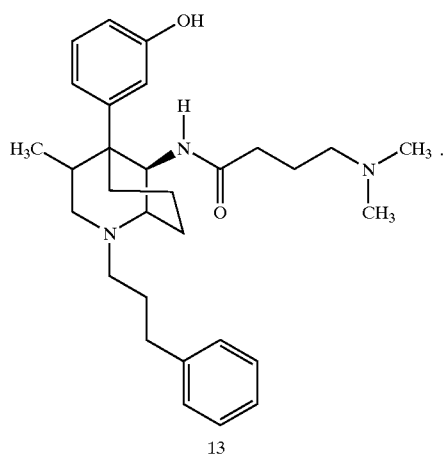
13

24. A pharmaceutical composition comprising:

an effective amount of a kappa opioid receptor antagonist and a physiologically acceptable carrier, wherein said kappa opioid receptor antagonist is a compound of formula 12 or 13

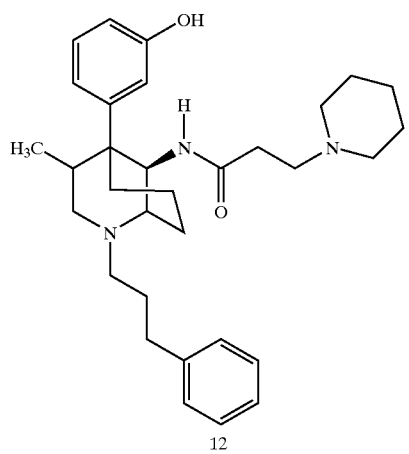
12

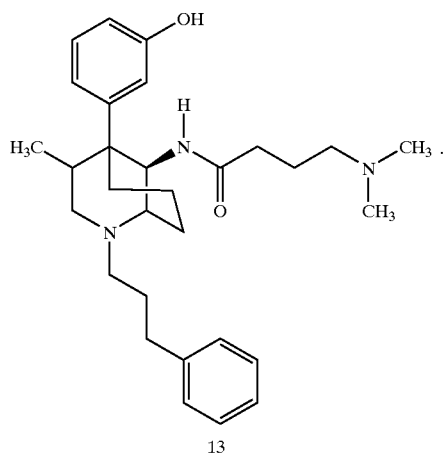
13

* * * * *

UNITED STATES PATENT AND TRADEMARK OFFICE
CERTIFICATE OF CORRECTION

PATENT NO. : 6,559,159 B2
DATED : May 6, 2003
INVENTOR(S) : F. Ivy Carroll

It is certified that error appears in the above-identified patent and that said Letters Patent is hereby corrected as shown below:

Column 1,
Line 20, "subtypes" should read -- subtypes, --
Line 46, "6)" should read -- 6). --

Column 4,
Line 45, 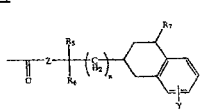 should read 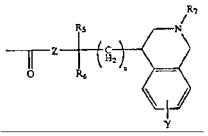

Column 6,
Line 50, 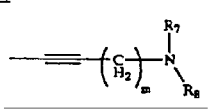 should read 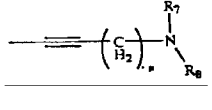

Column 10,
Line 5, 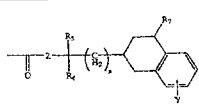 should read 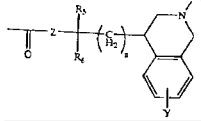

Column 12,
Line 5, 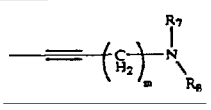 should read 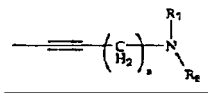

Line 42, "COOR$_9$" should read -- OCOR$_9$ --

Column 15,
Line 8, "heteroatom" should read -- heteroatom, --

Column 17,
Line 29, "41" should read -- $^{41}$ --
Line 41, "procedures." should read -- procedures, --
Line 44, "[$^{35}$SIGTP-γ-S" should read -- [$^{35}$S]GTP-γ-S --

Column 19,
Line 48, "Opiold" should read -- Opioid --

UNITED STATES PATENT AND TRADEMARK OFFICE
CERTIFICATE OF CORRECTION

PATENT NO. : 6,559,159 B2
DATED : May 6, 2003
INVENTOR(S) : F. Ivy Carroll

It is certified that error appears in the above-identified patent and that said Letters Patent is hereby corrected as shown below:

Column 20,
Line 17, "[3H]" should read -- [$^3$H] --
Line 21, "[$^{35}$SIGTP" should read -- [$^{35}$S]GTP --
Line 22, "U69.593" should read -- U69,593 --
Line 30, "tetrahydropyridine." should read -- tetrayhdropyridine, --

Column 21,
Line 24, "7.7.16" should read -- 7.16 --

Column 22,
Line 9, "270" should read -- 2.70 --
Line 40, "absolute" should read -- absolute, --
Line 55, "-1(1R" should read -- -[(1R --

Column 23,
Line 36, "azabicyclol3.3.1]" should read -- azabicyclo [3.3.1] --

Column 25,
Line 44, "275" should read -- 275, --
Line 52, "Nickander" should read -- Nickander, R. --
Lines 65-66, "*Harris, ...Inc.:*" should read -- Harris,...Inc.: --

Column 26,
Line 36, "1.3-" should read -- 1,3- --
Line 44, "K.," should read -- K. --
Line 61, "-dimethyl4-" should read -- -dimethyl-4- --

Column 29,
Line 20, 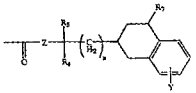 should read 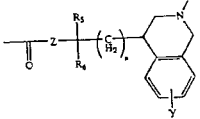

Column 31,
Line 13, 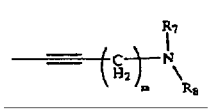 should read 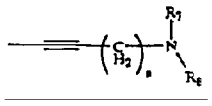

Line 50, "C3-8 alkynyl" should read -- $C_{3-8}$ alkynyl --
Line 62, "$C_{3-8}$ alkynyl, or $C_{1-8}$" should read -- $C_{3-8}$ alkynyl, or $C_{1-8}$ --

UNITED STATES PATENT AND TRADEMARK OFFICE
CERTIFICATE OF CORRECTION

PATENT NO.    : 6,559,159 B2
DATED         : May 6, 2003
INVENTOR(S)   : F. Ivy Carroll It is certified that error appears in the above-identified patent and that said Letters Patent is hereby corrected as shown below:

Column 33,
Line 66, "$C_{1-8}$ alkynyl" should read -- $C_{3-8}$ alkynyl --

Column 35,
Line 55, 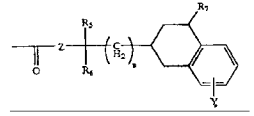 should read 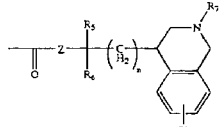

Column 37,
Line 55, 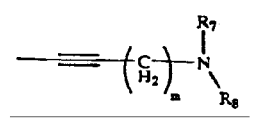 should read 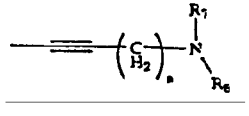

Column 38,
Line 31, "$COOR_9$" should read -- $OCOR_9$ --

Column 39,
Line 24, "$C_{1-8}$" should read -- $C_{3-8}$ --

Column 42,
Line 45, 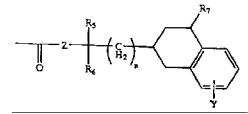 should read 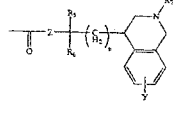

Column 44,
Line 35, 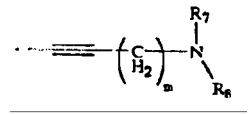 should read 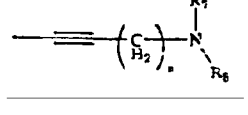

UNITED STATES PATENT AND TRADEMARK OFFICE
CERTIFICATE OF CORRECTION

PATENT NO.     : 6,559,159 B2                                           Page 4 of 5
DATED          : May 6, 2003
INVENTOR(S)    : F. Ivy Carroll It is certified that error appears in the above-identified patent and that said Letters Patent is hereby corrected as shown below:

Column 47,
Line 17, 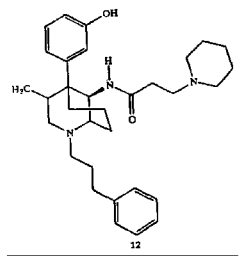 should read 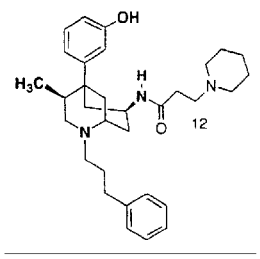

Line 35, 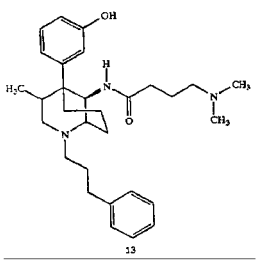 should read 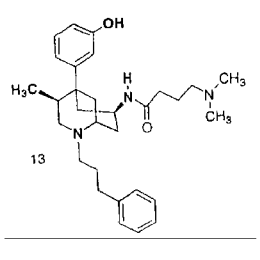

Line 55, 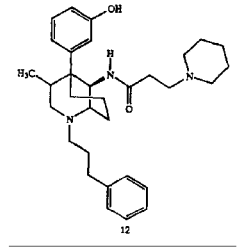 should read 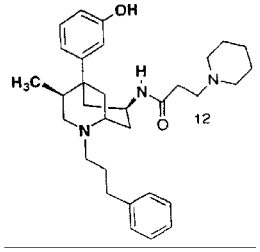

Column 48,
Line 10, 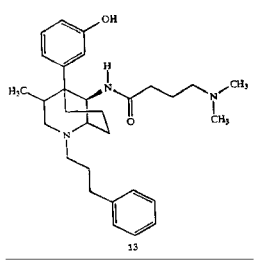 should read 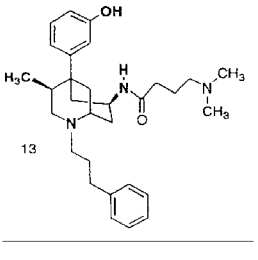

UNITED STATES PATENT AND TRADEMARK OFFICE
CERTIFICATE OF CORRECTION

PATENT NO. : 6,559,159 B2  
DATED : May 6, 2003  
INVENTOR(S) : F. Ivy Carroll

Page 5 of 5

It is certified that error appears in the above-identified patent and that said Letters Patent is hereby corrected as shown below:

Column 48 (cont'd),  
Line 35, 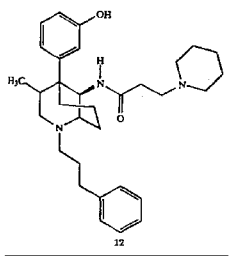 should read 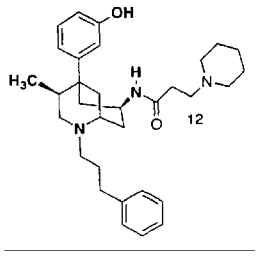

Line 53, 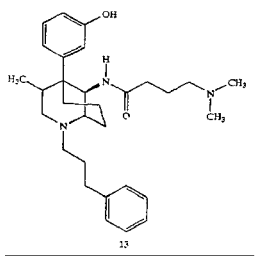 should read 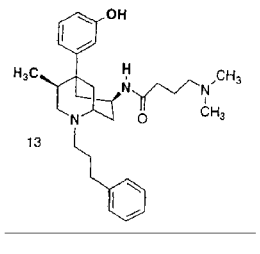

Signed and Sealed this

Third Day of August, 2004

JON W. DUDAS  
*Acting Director of the United States Patent and Trademark Office*